United States Patent
Linsell et al.

(10) Patent No.: US 7,399,863 B2
(45) Date of Patent: Jul. 15, 2008

(54) AMINO-SUBSTITUTED ETHYLAMINO $\beta_2$ ADRENERGIC RECEPTOR AGONISTS

(75) Inventors: Martin S. Linsell, San Mateo, CA (US); John R. Jacobsen, San Mateo, CA (US); Daisuke Roland Saito, Burlingame, CA (US)

(73) Assignee: Theravance, Inc., South San Francisco, CA (US)

( * ) Notice: Subject to any disclaimer, the term of this patent is extended or adjusted under 35 U.S.C. 154(b) by 580 days.

(21) Appl. No.: 10/946,544

(22) Filed: Sep. 21, 2004

(65) Prior Publication Data

US 2005/0113411 A1 May 26, 2005

Related U.S. Application Data

(60) Provisional application No. 60/505,685, filed on Sep. 22, 2003.

(51) Int. Cl.
C07D 215/38 (2006.01)
C07C 211/00 (2006.01)

(52) U.S. Cl. .................. 546/157; 564/306
(58) Field of Classification Search .......... 546/153, 546/157; 564/306
See application file for complete search history.

(56) References Cited

U.S. PATENT DOCUMENTS

| | | | |
|---|---|---|---|
| 3,875,233 A | 4/1975 | Bastian et al. |
| 4,021,485 A | 5/1977 | Schromm et al. |
| 4,894,219 A | 1/1990 | Baker et al. |
| 4,992,474 A | 2/1991 | Skidmore et al. |
| 5,223,614 A | 6/1993 | Schromm et al. |
| 5,434,304 A | 7/1995 | Trofast et al. |
| 5,750,701 A | 5/1998 | Beeley et al. |
| 6,268,533 B1 | 7/2001 | Gao et al. |
| 6,541,669 B1 | 4/2003 | Moran et al. |
| 6,576,793 B1 | 6/2003 | Moran et al. |
| 6,653,323 B2 | 11/2003 | Moran et al. |
| 6,670,376 B1 | 12/2003 | Moran et al. |
| 6,747,043 B2 | 6/2004 | Moran et al. |
| 6,759,398 B2 | 7/2004 | Biggadike |
| 6,825,220 B2 | 11/2004 | Jesudason et al. |
| 2002/0019378 A1 | 2/2002 | Angell et al. |
| 2002/0022625 A1 | 2/2002 | Walland et al. |
| 2002/0143034 A1 | 10/2002 | Taniguchi et al. |
| 2003/0229058 A1 | 12/2003 | Moran et al. |

(Continued)

FOREIGN PATENT DOCUMENTS

BE 849 794 4/1977

(Continued)

OTHER PUBLICATIONS

U.S. Appl. No. 11/033,198, filed Jan. 11, 2005, McKinnell et al.

(Continued)

*Primary Examiner*—D. Margaret Seaman
(74) *Attorney, Agent, or Firm*—Jeffrey A. Hagenah; Roberta P. Saxon

(57) ABSTRACT

The invention provides novel $\beta_2$ adrenergic receptor agonist compounds. The invention also provides pharmaceutical compositions comprising such compounds, methods of using such compounds to treat diseases associated with $\beta_2$ adrenergic receptor activity, and processes and intermediates useful for preparing such compounds.

13 Claims, 1 Drawing Sheet

2θ (degrees)

U.S. PATENT DOCUMENTS

| | | | |
|---|---|---|---|
| 2004/0059116 A1 | 3/2004 | Moran et al. | |
| 2004/0063755 A1 | 4/2004 | Moran et al. | |
| 2004/0157830 A1 | 8/2004 | Biggadike et al. | |
| 2004/0180876 A1 | 9/2004 | Biggadike et al. | |
| 2004/0186080 A1 | 9/2004 | Moran et al. | |
| 2004/0224982 A1 | 11/2004 | Axt et al. | |
| 2004/0242890 A1 | 12/2004 | Coe et al. | |
| 2004/0248985 A1 | 12/2004 | Stergiades et al. | |
| 2005/0272769 A1* | 12/2005 | Linsell | 514/312 |

FOREIGN PATENT DOCUMENTS

| | | |
|---|---|---|
| CH | 550 768 | 2/1972 |
| EP | 0 233 686 A2 | 8/1987 |
| EP | 0147 719 B1 | 7/1989 |
| EP | 0 196 849 A2 | 10/1996 |
| GB | 1040724 | 9/1966 |
| JP | 52-83379 | 7/1977 |
| JP | 52-83619 | 7/1977 |
| WO | WO 99/64035 A1 | 12/1999 |
| WO | WO 00/75114 A1 | 12/2000 |
| WO | WO 01/42193 A1 | 6/2001 |
| WO | WO 03/024439 A1 | 3/2003 |
| WO | WO 03/042160 A1 | 5/2003 |
| WO | WO 03/042164 A1 | 5/2003 |
| WO | WO 03/072539 A1 | 9/2003 |
| WO | WO 03/091204 A1 | 11/2003 |
| WO | WO 2004/016578 A2 | 2/2004 |

OTHER PUBLICATIONS

U.S. Appl. No. 10/627,555, filed May 8, 2003, Linsell et al.

Bompart et al., "Synthesis of new β-blocking analogs of bevantolol", Annales Pharmaceutiques Francaises, Volume Date 1984, 42(6), pp. 537-545 (1985) (In French with English abstract).

Bompart et al., "Synthesis of new β-blocker analogs of bevantolol or alprenolol", Annales Pharmaceutiques Francaises, Volume Date 1987, 45(5), pp. 379-387 (1988) (In French with English abstract).

Deyrup et al., "Structure-affinity profile of 8-hydroxycarbostyril-based agonists that dissociate slowly from the Beta2-adrenoceptor", Naunyn-Schmiedeberg's Arch Pharmacol (1999) 359:168-177.

Isogaya et al., "Binding Pockets of the $\beta_1$- and $\beta_2$-Adrenergic Receptors for Subtype-Selective Agonists"), Molecular Pharmacology, vol. 56, pp. 875-885 (1999).

Milecki et al., "Carbostyril Derivatives Having Potent β-Adrenergic Agonist Properties", J. Med. Chem, (1987), 30, 1563-1566.

Yokoi et al., "The Development of a Radioimmunoassay for Formoterol", Life Sciences, (1983) vol. 33, No. 17, pp. 1665-1672.

Yoshizaki et al., "Sympathomimetic Amines Having a Carbostyril Nucleus", J. Med. Chem., (1976), vol. 19, No. 9, pp. 1138-1142.

Office Action in U.S. Appl. No. 10/431,762, dated Apr. 17, 2006.

Office Action in U.S. Appl. No. 10/431,762, dated Sep. 26, 2006.

Office Action in U.S. Appl. No. 10/431,762, dated Mar. 14, 2007.

* cited by examiner

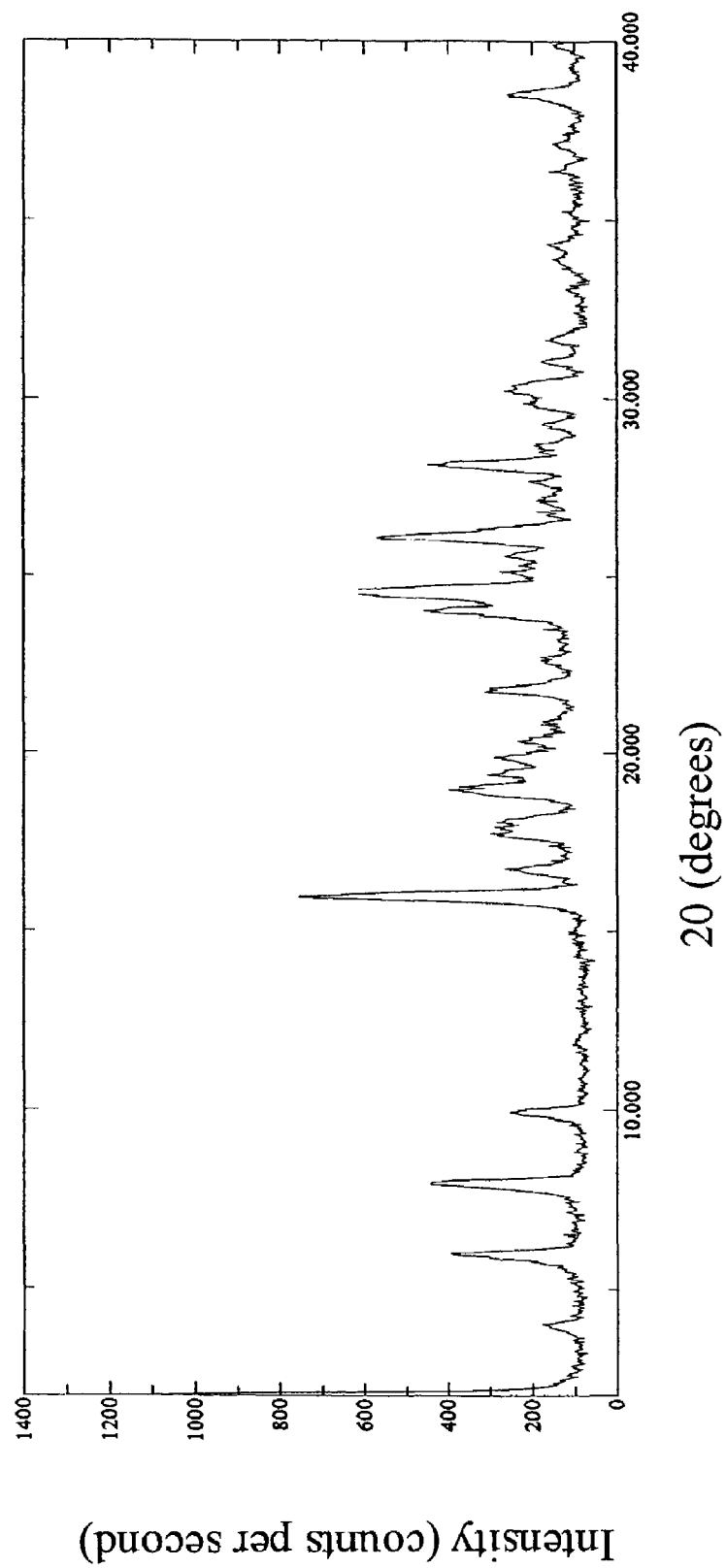

AMINO-SUBSTITUTED ETHYLAMINO β₂ ADRENERGIC RECEPTOR AGONISTS

CROSS-REFERENCE TO RELATED APPLICATIONS

This application claims the benefit of U.S. Provisional Application No. 60/505,685, filed on Sep. 22, 2003, the disclosure of which is incorporated herein by reference in its entirety.

FIELD OF THE INVENTION

The invention is directed to novel $\beta_2$ adrenergic receptor agonists. The invention is also directed to pharmaceutical compositions comprising such compounds, methods of using such compounds to treat diseases associated with $\beta_2$ adrenergic receptor activity, and processes and intermediates useful for preparing such compounds.

BACKGROUND OF THE INVENTION $\beta_2$ Adrenergic receptor agonists are recognized as effective drugs for the treatment of pulmonary diseases such as asthma and chronic obstructive pulmonary disease (including chronic bronchitis and emphysema). $\beta_2$ Adrenergic receptor agonists are also useful for treating pre-term labor, and are potentially useful for treating neurological disorders and cardiac disorders. In spite of the success that has been achieved with certain $\beta_2$ adrenergic receptor agonists, current agents possess less than desirable duration of action, potency, selectivity, and/or onset. Thus, there is a need for new $\beta_2$ adrenergic receptor agonists having improved properties, such as improved duration of action, potency, selectivity, and/or onset.

SUMMARY OF THE INVENTION

The invention provides novel compounds that possess $\beta_2$ adrenergic receptor agonist activity. Among other properties, compounds of the invention have been found to be potent and selective $\beta_2$ adrenergic receptor agonists. In addition, compounds of the invention have been found to possess a surprising and unexpectedly long duration of action, which allows for once-daily, or even less frequent, dosing.

Accordingly, this invention provides a compound of formula (I):

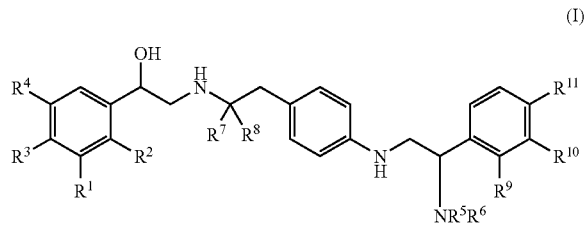

(I)

wherein:
each of $R^1$, $R^2$, $R^3$, and $R^4$ is independently selected from hydrogen, amino, halo, hydroxy, —CH$_2$OH and —NHCHO, or $R^1$ and $R^2$ taken together are —NHC(=O)CH=CH—, —CH=CHC(=O)NH—, —NHC(=O)S—, or —SC(=O)NH—;
each of $R^5$ and $R^6$ is independently selected from hydrogen, $C_{1-6}$alkyl, —C(=O)R$^d$, $C_{2-6}$alkenyl, $C_{2-6}$alkynyl, and $C_{3-6}$cycloalkyl, wherein each $C_{1-6}$alkyl, $C_{2-6}$alkenyl, $C_{2-6}$alkynyl, and $C_{3-6}$cycloalkyl is optionally substituted with one or more substituents independently selected from aryl, heteroaryl, heterocyclyl, —OR$^a$, and —NR$^b$R$^c$, wherein each aryl, heteroaryl, and heterocyclyl is optionally substituted with one or more substituents independently selected from —OR$^a$ and —NR$^b$R$^c$,
or $R^5$ and $R^6$ together with the nitrogen atom to which they are attached form a heterocyclic ring having from 5 to 7 ring atoms and containing 1 or 2 heteroatoms independently selected from oxygen, nitrogen, and sulfur, wherein sulfur is optionally substituted with one or two oxygens;
each of $R^7$ and $R^8$ is independently hydrogen or $C_{1-6}$alkyl;
each of $R^9$, $R^{10}$, and $R^{11}$ is independently selected from hydrogen, $C_{1-6}$alkyl, aryl, halo, —OR$^a$, and —NR$^b$R$^c$;
$R^d$ is hydrogen or $C_{1-3}$alkyl, optionally substituted with one or more substituents independently selected from —OR$^a$, —NR$^b$R$^c$, piperidinyl and pyrrolidinyl; and
each R$^a$, R$^b$, and R$^c$ is independently hydrogen or $C_{1-3}$alkyl;
or a pharmaceutically-acceptable salt or solvate or stereoisomer thereof.

The invention also provides pharmaceutical compositions comprising a compound of the invention and a pharmaceutically-acceptable carrier. The invention further provides combinations comprising a compound of the invention and one or more other therapeutic agents and pharmaceutical compositions comprising such combinations.

The invention also provides a method of treating a disease or condition associated with $\beta_2$ adrenergic receptor activity (e.g. a pulmonary disease, such as asthma or chronic obstructive pulmonary disease, pre-term labor, a neurological disorder, a cardiac disorder, or inflammation) in a mammal, comprising administering to the mammal, a therapeutically effective amount of a compound of the invention. The invention further provides a method of treatment comprising administering a therapeutically effective amount of a combination of a compound of the invention together with one or more other therapeutic agents.

The invention also provides a method of treating a disease or condition associated with $\beta_2$ adrenergic receptor activity in a mammal, comprising administering to the mammal, a therapeutically effective amount of a pharmaceutical composition of the invention.

The compounds of the invention can also be used as research tools, i.e. to study biological systems or samples, or to discover new $\beta_2$ adrenergic receptor agonists. Accordingly, in one of its method aspects, the invention is directed to a method of agonizing a $\beta_2$ adrenergic receptor in a biological system or sample, the method comprising contacting a biological system or sample comprising a $\beta_2$ adrenergic receptor with $\beta_2$ adrenergic receptor-agonizing amount of a compound of formula (I), or a pharmaceutically acceptable salt or solvate or stereoisomer thereof.

In separate and distinct aspects, the invention also provides synthetic processes and intermediates described herein, which are useful for preparing compounds of the invention.

The invention also provides a compound of the invention as described herein for use in medical therapy, as well as the use of a compound of the invention in the manufacture of a formulation or medicament for treating a disease or condition associated with $\beta_2$ adrenergic receptor activity, e.g. a pulmonary disease, such as asthma or chronic obstructive pulmonary disease, pre-term labor, a neurological disorder, a cardiac disorder, or inflammation, in a mammal.

BRIEF DESCRIPTION OF THE DRAWING

The invention is illustrated by reference to the accompanying drawing which shows a powder x-ray diffraction pattern of N-{2-[4-((R)-2-hydroxy-2-phenylethylamino)phenyl]ethyl}-(R)-2-hydroxy-2-(3-formamido-4-hydroxyphenyl)ethylamine hydrochloride.

DETAILED DESCRIPTION OF THE INVENTION

The invention provides novel amino-substituted ethylamino β$_2$ adrenergic receptor agonists of formula (I), or pharmaceutically-acceptable salts or solvates or stereoisomers thereof. The following exemplary and preferred values for radicals, substituents, and ranges, are for illustration only; they do not exclude other defined values or other values within defined ranges for the radicals and substituents.

Examples of particular values of $R^1$ are halo, —CH$_2$OH, and —NHCHO, including chloro, —CH$_2$OH, and —NHCHO.

Another particular value for $R^1$ is —CH$_2$OH or —NHCHO.

A particular value for $R^2$ is hydrogen.

A particular value for $R^1$ and $R^2$ is $R^1$ and $R^2$ taken together are —NHC(=O)CH=CH— or —CH=CHC(=O)NH—.

Examples of particular values for $R^3$ are hydroxy and amino.

Examples of particular values for $R^4$ are hydrogen and halo, including hydrogen and chloro.

One group of compounds of formula (I) are compounds wherein $R^1$ is —NHCHO, $R^3$ is hydroxy, and $R^2$ and $R^4$ are each hydrogen.

Another group of compounds of formula (I) are compounds wherein $R^1$ and $R^2$ taken together are —NHC(=O)CH=CH— or —CH=CHC(=O)NH—, $R^3$ is hydroxy, and $R^4$ is hydrogen.

Another specific value for $R^1$, $R^2$, $R^3$, and $R^4$ is $R^1$ is —CH$_2$OH, $R^3$ is hydroxy, and $R^2$ and $R^4$ are each hydrogen.

Yet another specific value for $R^1$, $R^2$, $R^3$, and $R^4$ is $R^1$ and $R^4$ are chloro, $R^3$ is amino, and $R^2$ is hydrogen.

Examples of particular values for $R^5$ and $R^6$ are $R^5$ and $R^6$ are each independently selected from hydrogen, C$_{1-6}$alkyl, and C$_{3-6}$cycloalkyl, wherein each C$_{1-6}$alkyl is optionally substituted with one or more substituents independently selected from heterocyclyl, —OR$^a$, and —NR$^b$R$^c$. Other examples of $R^5$ and $R^6$ are $R^5$ and $R^6$ together with the nitrogen atom to which they are attached form a heterocyclic ring having from 5 to 7 ring atoms and containing 1 or 2 heteroatoms independently selected from oxygen, nitrogen, and sulfur.

In one embodiment, $R^5$ and $R^6$ are each independently hydrogen or C$_{1-3}$alkyl, wherein each C$_{1-3}$alkyl is optionally substituted with one substituent independently selected from hydroxyl, amino, piperidinyl, and pyrrolidinyl. In another embodiment, $R^5$ and $R^6$ together with the nitrogen atom to which they are attached form a morpholinyl or piperidinyl ring.

In yet another embodiment, $R^5$ and $R^6$ are each independently hydrogen or C$_{1-3}$alkyl.

A particular value for $R^7$ is hydrogen.

A particular value for $R^8$ is hydrogen.

Examples of particular values for $R^9$ are hydrogen, halo and —OR$^a$ where R$^a$ is hydrogen or C$_{1-3}$alkyl.

Another example of particular values for $R^9$ is hydroxy and methoxy.

Another particular value for $R^9$ is hydrogen.

Examples of particular values for $R^{10}$ are hydrogen, halo and —OR$^a$ where R$^a$ is hydrogen or C$_{1-3}$alkyl.

Another example of particular values for $R^{10}$ is hydroxy and methoxy.

Another particular value for $R^{10}$ is hydrogen.

Examples of particular values for $R^{11}$ are hydrogen, halo and —OR$^a$ where R$^a$ is hydrogen or C$_{1-3}$alkyl.

Another example of particular values for $R^{11}$ is hydroxy and methoxy.

Another particular value for $R^{11}$ is hydrogen.

In one embodiment of the invention, a compound of formula (I) is a compound of formula (II):

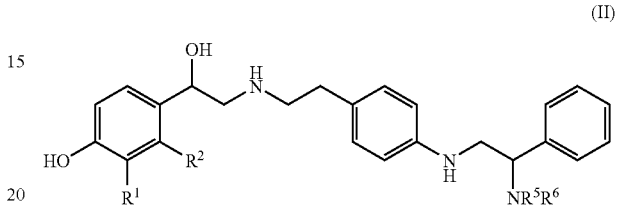

(II)

wherein:
$R^1$ is —CH$_2$OH or —NHCHO, and $R^2$ is hydrogen; or $R^1$ and $R^2$ taken together are —NHC(=O)CH=CH— or —CH=CHC(=O)NH—;

each of $R^5$ and $R^6$ is independently selected from hydrogen, C$_{1-6}$alkyl, C$_{2-6}$alkenyl, C$_{2-6}$alkynyl, and C$_{3-6}$cycloalkyl, wherein each C$_{1-6}$alkyl, C$_{2-6}$alkenyl, C$_{2-6}$alkynyl, and C$_{3-6}$cycloalkyl is optionally substituted with one or more substituents independently selected from aryl, heteroaryl, heterocyclyl, —OR$^a$, and —NR$^b$R$^c$, wherein each aryl, heteroaryl, and heterocyclyl is optionally substituted with one or more substituents independently selected from —OR$^a$ and —NR$^b$R$^c$, or $R^5$ and $R^6$ together with the nitrogen atom to which they are attached form a heterocyclic ring having from 5 to 7 ring atoms and containing 1 or 2 heteroatoms independently selected from oxygen, nitrogen, and sulfur, wherein sulfur is optionally substituted with one or two oxygens; and each R$^a$, R$^b$, and R$^c$ is independently hydrogen or C$_{1-3}$alkyl;

or a pharmaceutically-acceptable salt or solvate or stereoisomer thereof.

One group of compounds of formula (II) are those in which each of $R^5$ and $R^6$ is independently selected from hydrogen, C$_{1-6}$alkyl, and C$_{3-6}$cycloalkyl, wherein each C$_{1-6}$alkyl is optionally substituted with one or more substituents independently selected from heterocyclyl, —OR$^a$, and —NR$^b$R$^c$, or $R^5$ and $R^6$ together with the nitrogen atom to which they are attached form a heterocyclic ring having from 5 to 7 ring atoms and containing 1 or 2 heteroatoms independently selected from oxygen, nitrogen, and sulfur.

In another group of compounds of formula (II), each of $R^5$ and $R^6$ is independently hydrogen or C$_{1-3}$alkyl, wherein each C$_{1-3}$alkyl is optionally substituted with one substituent independently selected from hydroxyl, amino, piperidinyl, and pyrrolidinyl; or $R^5$ and $R^6$ together with the nitrogen atom to which they are attached form a morpholinyl or piperidinyl ring. In yet another group of compounds of formula (II), each of $R^5$ and $R^6$ is hydrogen or C$_{1-3}$alkyl.

Particular mention may be made of the following compounds:

5-((R)-2-{2-[4-((R)-2-amino-2-phenylethylamino)phenyl]ethylamino}-1-hydroxy-ethyl)-8-hydroxy-1H-quinolin-2-one:

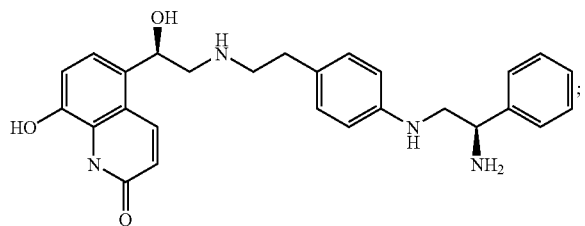

N-[5-((R)-2-{2-[4-((R)-2-amino-2-phenylethylamino)phenyl]ethylamino}-1-hydroxyethyl)-2-hydroxyphenyl]formamide:

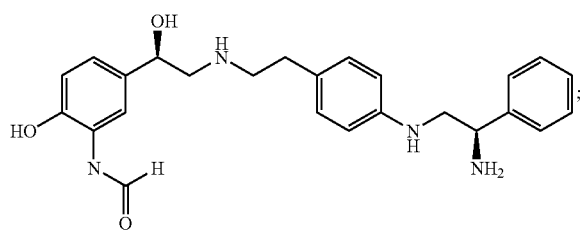

5-((R)-2-{2-[4-((S)-2-amino-2-phenylethylamino)phenyl]ethylamino}-1-hydroxy-ethyl)-8-hydroxy-1H-quinolin-2-one;
N-[5-((R)-2-{2-[4-((S)-2-amino-2-phenylethylamino)phenyl]ethylamino}-1-hydroxyethyl)-2-hydroxyphenyl]formamide;
5-((R)-2-{2-[4-((R)-2-methylamino-2-phenylethylamino)phenyl]ethylamino}-1-hydroxyethyl)-8-hydroxy-1H-quinolin-2-one;
5-((R)-2-{2-[4-((R)-2-dimethylamino-2-phenylethylamino)phenyl]ethylamino}-1-hydroxyethyl)-8-hydroxy-1H-quinolin-2-one;
N-[5-((R)-2-{2-[4-((R)-2-methylamino-2-phenylethylamino)phenyl]ethylamino}-1-hydroxyethyl)-2-hydroxyphenyl]formamide;
N-[5-((R)-2-{2-[4-((R)-2-dimethylamino-2-phenylethylamino)phenyl]-ethylamino}-1-hydroxyethyl)-2-hydroxyphenyl]formamide;
5-((R)-2-{2-[4-((S)-2-methylamino-2-phenylethylamino)phenyl]ethylamino}-1-hydroxyethyl)-8-hydroxy-1H-quinolin-2-one;
5-((R)-2-{2-[4-((S)-2-dimethylamino-2-phenylethylamino)phenyl]ethylamino}-1-hydroxyethyl)-8-hydroxy-1H-quinolin-2-one;
N-[5-((R)-2-{2-[4-((S)-2-methylamino-2-phenylethylamino)phenyl]ethylamino}-1-hydroxyethyl)-2-hydroxyphenyl]formamide; and
N-[5-((R)-2-{2-[4-((S)-2-dimethylamino-2-phenylethylamino)phenyl]-ethylamino}-1-hydroxyethyl)-2-hydroxyphenyl]formamide; where the chemical nomenclature conforms to that of the automatic naming program AutoNom, as provided by MDL Information Systems, GmbH (Frankfurt, Germany).

As illustrated above, the compounds of the invention contain one or more chiral centers. Accordingly, the invention includes racemic mixtures, pure stereoisomers (i.e. individual enantiomers or diastereomers), and stereoisomer-enriched mixtures of such isomers, unless otherwise indicated. When a particular stereoisomer is shown, it will be understood by those skilled in the art, that minor amounts of other stereoisomers may be present in the compositions of this invention unless otherwise indicated, provided that the utility of the composition as a whole is not eliminated by the presence of such other isomers.

In particular, compounds of the invention contain a chiral center at the alkylene carbon in formulas (I) and (II) to which the hydroxy group is attached. When a mixture of stereoisomers is employed, it is advantageous for the amount of the stereoisomer with the (R) orientation at the chiral center bearing the hydroxy group to be greater than the amount of the corresponding (S) stereoisomer. When comparing stereoisomers of the same compound, the (R) stereoisomer is preferred over the (S) stereoisomer.

Definitions

When describing the compounds, compositions and methods of the invention, the following terms have the following meanings, unless otherwise indicated.

The term "alkyl" means a monovalent saturated hydrocarbon group which may be linear or branched or combinations thereof. Representative alkyl groups include, by way of example, methyl, ethyl, n-propyl, isopropyl, n-butyl, sec-butyl, isobutyl, tert-butyl, n-pentyl, n-hexyl, n-heptyl, n-octyl, n-nonyl, n-decyl and the like.

When a specific number of carbon atoms is intended for a particular term used herein, the number of carbon atoms is shown preceding the term. For example, the term "$C_{1-6}$alkyl" means an alkyl group having from 1 to 6 carbon atoms.

The term "alkenyl" means a monovalent unsaturated hydrocarbon group containing at least one carbon-carbon double bond, typically 1 or 2 carbon-carbon double bonds, and which may be linear or branched or combinations thereof. Representative alkenyl groups include, by way of example, vinyl, allyl, isopropenyl, but-2-enyl, n-pent-2-enyl, n-hex-2-enyl, n-hept-2-enyl, n-oct-2-enyl, n-non-2-enyl, n-dec-4-enyl, n-dec-2,4-dienyl and the like.

The term "alkynyl" means a monovalent unsaturated hydrocarbon group containing at least one carbon-carbon triple bond, typically 1 carbon-carbon triple bond, and which may be linear or branched or combinations thereof. Representative alkynyl groups include, by way of example, ethynyl, propargyl, but-2-ynyl and the like.

The term "cycloalkyl" means a monovalent saturated carbocyclic group which may be monocyclic or multicyclic. Representative cycloalkyl groups include, by way of example, cyclopropyl, cyclobutyl, cyclopentyl, cyclohexyl, cycloheptyl, cyclooctyl, and the like.

The term "aryl" means a monovalent aromatic hydrocarbon having a single ring (i.e. phenyl) or fused rings (i.e. napthalene). Unless otherwise defined, such aryl groups typically contain from 6 to 10 carbon ring atoms. Representative aryl groups include, by way of example, phenyl, and napthalene-1-yl, napthalene-2-yl and the like.

The term "heteroaryl" means a monovalent aromatic group having a single ring or two fused rings and containing in the ring at least one heteroatom (typically 1 to 3 heteroatoms) selected from nitrogen, oxygen, and sulfur. Unless otherwise defined, such heteroaryl groups typically contain from 5 to 10 atoms total ring atoms. Representative heteroaryl groups include, by way of example, pyrroyl, isoxazolyl, isothiazolyl, pyrazolyl, pyridyl (or, equivalently, pyridinyl), oxazolyl, oxadiazolyl, thiadiazolyl, thiazolyl, imidazolyl, triazolyl, tetrazolyl, furanyl, triazinyl, thienyl, pyrimidyl, pyridazinyl, pyrazinyl, benzoxazolyl, benzothiazolyl, benzimidazolyl, benzofuranyl, benzothiophenyl, quinolyl, indolyl, isoquinolyl and the like, where the point of attachment is at any available carbon or nitrogen ring atom.

The term "heterocyclyl" or "heterocyclic ring" means a monovalent saturated or partially unsaturated cyclic non-aromatic group, which may be monocyclic or multicyclic (i.e., fused or bridged), and which contains at least one heteroatom (typically 1 to 3 heteroatoms) selected from nitrogen, oxygen, and sulfur. Unless otherwise defined, such heterocyclyl groups typically contain from 5 to 10 total ring atoms. Representative heterocyclyl groups include, by way of example, pyrrolidinyl, piperidinyl, piperazinyl, imidazolidinyl, morpholinyl, indolin-3-yl, 2-imidazolinyl, 1,2,3,4-tetrahydroisoquinolin-2-yl, quinuclidinyl, and the like.

The term "halo" means fluoro, chloro, bromo or iodo.

The term "amino" means —NH$_2$.

The term "therapeutically effective amount" means an amount sufficient to effect treatment when administered to a patient in need of treatment.

The term "treatment" as used herein means the treatment of a disease or medical condition in a patient, such as a mammal (particularly a human) which includes:
 (a) preventing the disease or medical condition from occurring, i.e., prophylactic treatment of a patient;
 (b) ameliorating the disease or medical condition, i.e., eliminating or causing regression of the disease or medical condition in a patient;
 (c) suppressing the disease or medical condition, i.e., slowing or arresting the development of the disease or medical condition in a patient; or
 (d) alleviating the symptoms of the disease or medical condition in a patient.

The phrase "disease or condition associated with $\beta_2$ adrenergic receptor activity" includes all disease states and/or conditions that are acknowledged now, or that are found in the future, to be associated with $\beta_2$ adrenergic receptor activity. Such disease states include, but are not limited to, pulmonary diseases, such as asthma and chronic obstructive pulmonary disease (including chronic bronchitis and emphysema), as well as neurological disorders and cardiac disorders. $\beta_2$ adrenergic receptor activity is also known to be associated with pre-term labor (see U.S. Pat. No. 5,872,126) and some types of inflammation (see International Patent Application Publication Number WO 99/30703 and U.S. Pat. No. 5,290,815).

The term "pharmaceutically-acceptable salt" means a salt prepared from a base or acid which is acceptable for administration to a patient, such as a mammal. Such salts can be derived from pharmaceutically-acceptable inorganic or organic bases and from pharmaceutically-acceptable inorganic or organic acids.

Salts derived from pharmaceutically-acceptable acids include, but are not limited to, acetic, benzenesulfonic, benzoic, camphosulfonic, citric, ethanesulfonic, fumaric, gluconic, glutamic, hydrobromic, hydrochloric, lactic, maleic, malic, mandelic, methanesulfonic, mucic, nitric, pantothenic, phosphoric, succinic, sulfuric, tartaric, p-toluenesulfonic, xinafoic (1-hydroxy-2-naphthoic acid) and the like. Particularly preferred are salts derived from fumaric, hydrobromic, hydrochloric, acetic, sulfuric, methanesulfonic, xinafoic, and tartaric acids.

Salts derived from pharmaceutically-acceptable inorganic bases include aluminum, ammonium, calcium, copper, ferric, ferrous, lithium, magnesium, manganic, manganous, potassium, sodium, zinc and the like. Particularly preferred are ammonium, calcium, magnesium, potassium and sodium salts. Salts derived from pharmaceutically-acceptable organic bases include salts of primary, secondary and tertiary amines, including substituted amines, cyclic amines, naturally-occurring amines and the like, such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperadine, polyamine resins, procaine, purines, theobromine, triethylamine, trimethylamine, tripropylamine, tromethamine and the like.

The term "solvate" means a complex or aggregate formed by one or more molecules of a solute, i.e. a compound of the invention or a pharmaceutically-acceptable salt thereof, and one or more molecules of a solvent. Such solvates are typically crystalline solids having a substantially fixed molar ratio of solute and solvent. Representative solvents include by way of example, water, methanol, ethanol, isopropanol, acetic acid, and the like. When the solvent is water, the solvate formed is a hydrate.

It will be appreciated that the term "or a pharmaceutically-acceptable salt or solvate of stereoisomer thereof" is intended to include all permutations of salts, solvates and stereoisomers, such as a solvate of a pharmaceutically-acceptable salt of a stereoisomer of a compound of formula (I).

The term "leaving group" means a functional group or atom which can be displaced by another functional group or atom in a substitution reaction, such as a nucleophilic substitution reaction. By way of example, representative leaving groups include chloro, bromo and iodo groups; sulfonic ester groups, such as mesylate, tosylate, brosylate, nosylate and the like; and acyloxy groups, such as acetoxy, trifluoroacetoxy and the like.

The term "amino-protecting group" means a protecting group suitable for preventing undesired reactions at an amino nitrogen. Representative amino-protecting groups include, but are not limited to, formyl; acyl groups, for example alkanoyl groups, such as acetyl; alkoxycarbonyl groups, such as tert-butoxycarbonyl (Boc); arylmethoxycarbonyl groups, such as benzyloxycarbonyl (Cbz) and 9-fluorenylmethoxycarbonyl (Fmoc); arylmethyl groups, such as benzyl (Bn), trityl (Tr), and 1,1-di-(4'-methoxyphenyl)methyl; silyl groups, such as trimethylsilyl (TMS) and tert-butyldimethylsilyl (TBS); and the like.

The term "hydroxy-protecting group" means a protecting group suitable for preventing undesired reactions at a hydroxy group. Representative hydroxy-protecting groups include, but are not limited to, alkyl groups, such as methyl, ethyl, and tert-butyl; acyl groups, for example alkanoyl groups, such as acetyl; arylmethyl groups, such as benzyl (Bn), p-methoxybenzyl (PMB), 9-fluorenylmethyl (Fm), and diphenylmethyl (benzhydryl, DPM); silyl groups, such as trimethylsilyl (TMS) and tert-butyldimethylsilyl (TBS); and the like.

General Synthetic Procedures

Compounds of the invention can be prepared from readily available starting materials using the following general methods and procedures. Although a particular aspect of the present invention is illustrated in the schemes below, those skilled in the art will recognize that all aspects of the present invention can be prepared using the methods described herein or by using other methods, reagents and starting materials known to those skilled in the art. It will also be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization procedures.

Additionally, as will be apparent to those skilled in the art, conventional protecting groups may be necessary to prevent certain functional groups from undergoing undesired reactions. The choice of a suitable protecting group for a particular functional group, as well as suitable conditions for protection and deprotection, are well known in the art. For example, numerous protecting groups, and their introduction and removal, are described in T. W. Greene and G. M. Wuts, *Protecting Groups in Organic Synthesis*, Third Edition, Wiley, New York, 1999, and references cited therein.

In one method of synthesis, compounds of formulas (I) and (II) are prepared as illustrated in Scheme A. (The substituents and variables shown in the following schemes have the definitions provided above unless otherwise indicated.)

3. Typically, this reaction is conducted in a polar, aprotic solvent in the presence of base with heating. The protecting group $P^1$ is typically a silyl protecting group, which is typically removed from the intermediate of formula 3 using a fluoride or acid reagent, to provide an intermediate of formula 4. The protecting group $P^2$ is typically a benzyl protecting group, which is typically removed from the intermediate of formula 4 by hydrogenation using a palladium on carbon catalyst, to provide the product.

The compounds of formula 1 employed in the reactions described in this application are readily prepared by procedures known in the art, and described, for example, in U.S. Pat. Nos. 6,653,323 B2 and 6,670,376 B1, which are incorporated herein by reference, and references therein. Intermediate 2 is prepared from readily available starting materials, for example, by procedures illustrated in Scheme B.

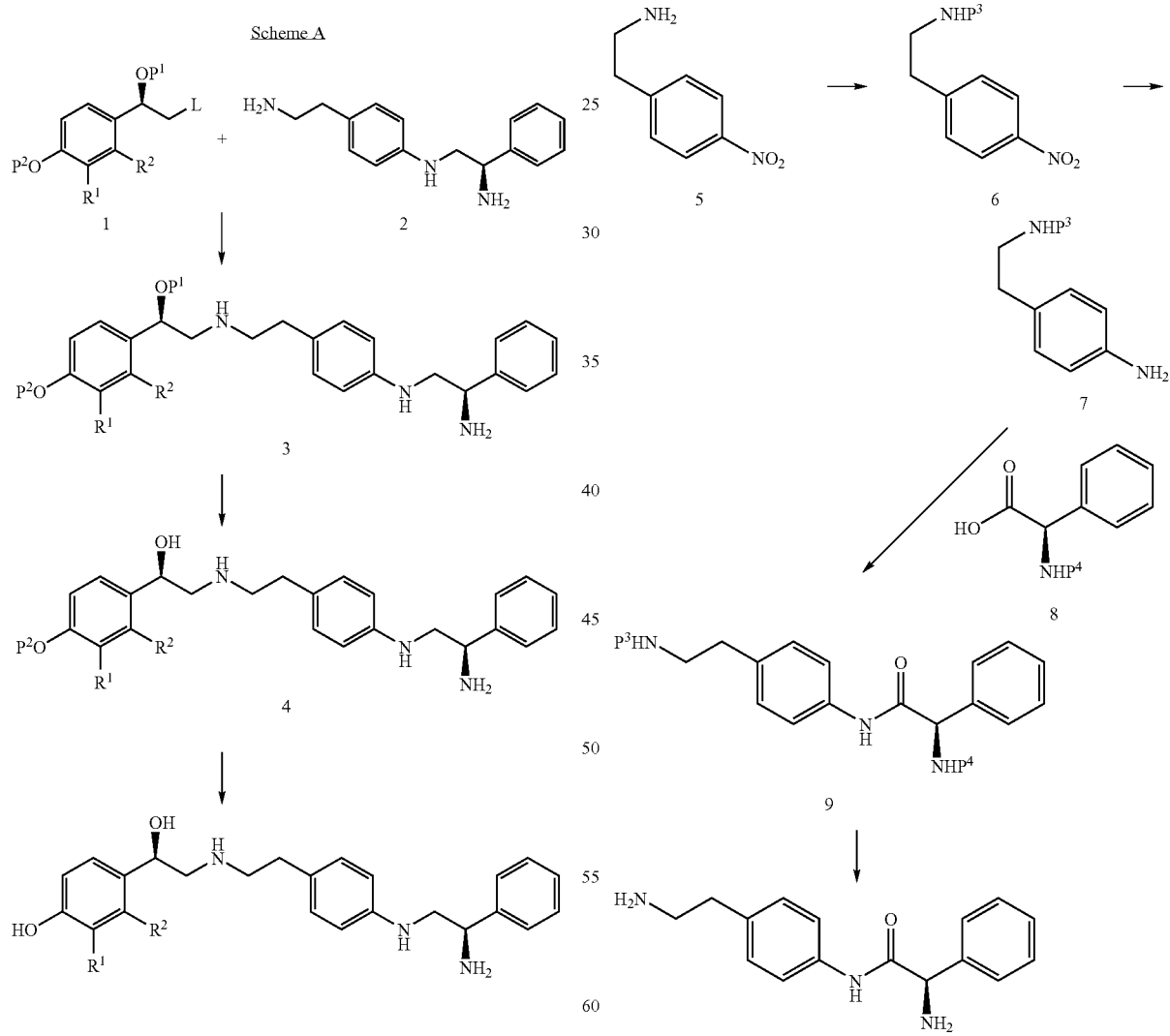

where $P^1$ represents a hydroxy-protecting group, $P^2$ represents a hydroxy-protecting group, and L represents a leaving group, such as bromo.

As shown in Scheme A, a compound of formula 1 is first reacted with (R)—$N^2$-[4-(2-aminoethyl)phenyl]-1-phenylethane-1,2-diamine (2) to provide an intermediate of formula -continued

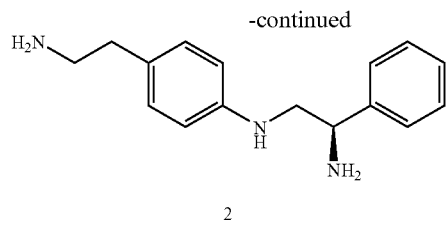

2

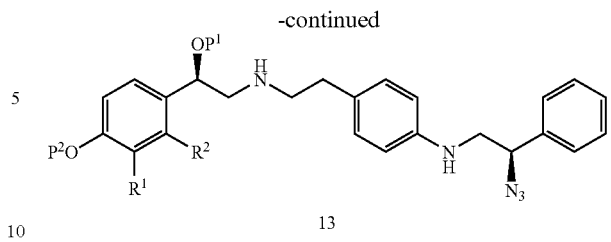

13

In Scheme B, P³ represents an amino-protecting group and P⁴ represents an amino-protecting group.

As illustrated in Scheme B, a protecting group, P³, is added to the amino nitrogen of 2-(4-nitrophenyl)ethylamine, 5, to provide an intermediate of formula 6. Protecting group P³ is typically a tert-butoxycarbonyl (Boc) group, which is typically added by reaction of di-tert-butyl dicarbonate (Boc₂O) under basic conditions. The intermediate 6 is reduced to provide an intermediate of formula 7. Reduction of the intermediate 6 is typically effected by hydrogenation using a palladium on carbon catalyst. The amine of intermediate 7 is coupled with the protected phenyl glycine 8 to provide an intermediate of formula 9. The coupling of the intermediate 7 with 8 can be effected using a peptide coupling agent, for example, 1-[3-(dimethylamino)propyl]-3-ethylcarbodiimide (EDC), and may employ a catalyst, for example, 1-hydroxybenzotriazole hydrate (HOBT) or 1-hydroxy-7-azabenzotriazole hydrate (HOAT). Intermediate 9 is deprotected, typically under acidic conditions, to provide an intermediate of formula 10, which is reduced, typically using a borane reductant, to form (R)—N²-[4-(2-aminoethyl)phenyl]-1-phenylethane-1,2-diamine (2).

The preparation of intermediate 2 is further described in Example 1, parts a-e, below.

Alternatively, compounds of the invention can be prepared as illustrated in Scheme C.

Scheme C

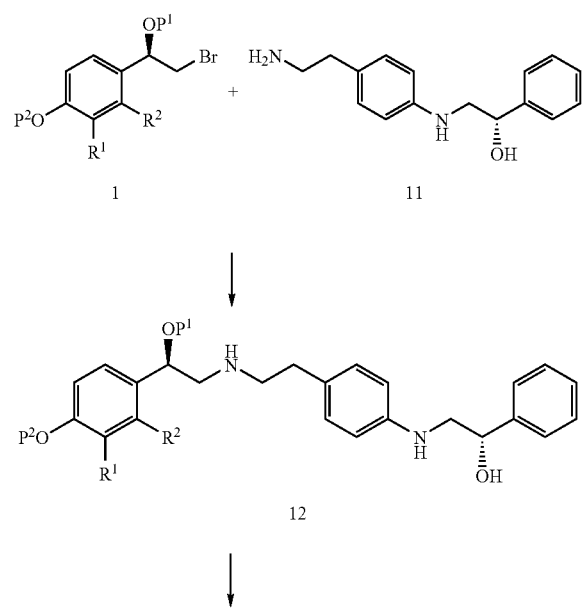

According to Scheme C, intermediate 1 is coupled with (S)-2-[4-(2-aminoethyl)-phenylamino]-1-phenylethanol (11) to provide an intermediate of formula 12. Typically, this reaction is conducted in a polar, aprotic solvent in the presence of base with heating. Intermediate 12 is reacted with a reagent such as diphenylphosphoryl azide, which converts the alcohol to a leaving group and provides a nucleophilic azide anion to provide the intermediate of formula 13. Alternatively, two-reagent systems can be used to convert intermediate 12 to the azide 13. Next, the protecting group P¹, which is typically a silyl protecting group, is removed, typically by use of a fluoride or acid reagent, to provide an intermediate of formula 14. The product can be provided by simultaneous hydrogenation of the azide and deprotection of the protecting group P² of the intermediate of formula 14, when P² is a group, such as benzyl, that is removed by hydrogenation. If the protecting group P² is not labile to hydrogenation, an additional deprotection step is required.

Intermediate 11 is readily prepared by the reaction of 2-(4-aminophenyl)ethylamine with chiral styrene oxide, as described in Example 3, part a, below.

Further details regarding specific reaction condition and other procedures for preparing representative compounds of the invention or intermediate thereto are described in the Examples below.

Accordingly, in a method aspect, the invention provides a process for preparing a compound of formula (I), or a salt or stereoisomer or protected derivative thereof, the process comprising:

reacting a compound of formula (III):

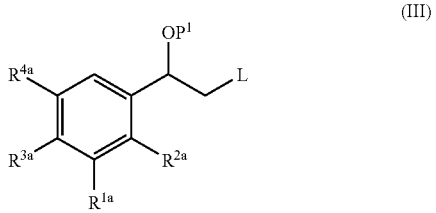

wherein $P^1$ is a hydroxy-protecting group, L is a leaving group, each of $R^{1a}$, $R^{2a}$, $R^{3a}$, and $R^{4a}$ is independently defined to be the same as $R^1$, $R^2$, $R^3$, and $R^4$ in formula (I), or $-OP^2$, wherein $P^2$ is a hydroxy-protecting group, with a compound of formula (IV):

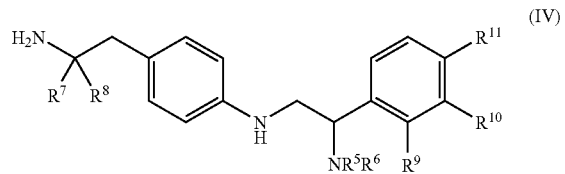

wherein $R^5$, $R^6$, $R^7$, $R^8$, $R^9$, $R^{10}$, and $R^{11}$ are defined as in formula (I), to provide a compound of formula (V):

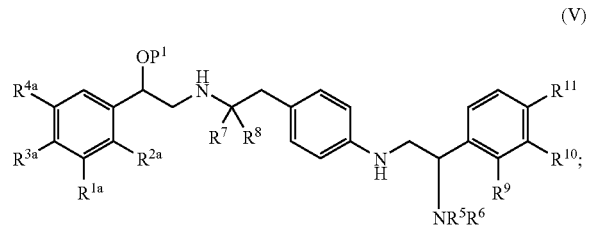

removing the protecting group $P^1$ to provide a compound of formula (VI):

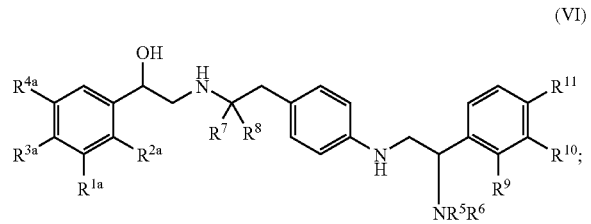

when any of $R^{1a}$, $R^{2a}$, $R^{3a}$, or $R^{4a}$ is $-OP^2$, removing the protecting group $P^2$ to provide a compound of formula (I), or a salt or stereoisomer thereof.

Pharmaceutical Compositions

The invention also provides pharmaceutical compositions comprising a compound of the invention. Accordingly, the compound, preferably in the form of a pharmaceutically-acceptable salt, can be formulated for any suitable form of administration, such as oral or parenteral administration, or administration by inhalation.

By way of illustration, the compound can be admixed with conventional pharmaceutical carriers and excipients and used in the form of powders, tablets, capsules, elixirs, suspensions, syrups, wafers, and the like. Such pharmaceutical compositions will contain from about 0.05 to about 90% by weight of the active compound, and more generally from about 0.1 to about 30%. The pharmaceutical compositions may contain common carriers and excipients, such as cornstarch or gelatin, lactose, magnesium sulfate, magnesium stearate, sucrose, microcrystalline cellulose, kaolin, mannitol, dicalcium phosphate, sodium chloride, and alginic acid. Disintegrators commonly used in the formulations of this invention include croscarmellose, microcrystalline cellulose, cornstarch, sodium starch glycolate and alginic acid.

A liquid composition will generally consist of a suspension or solution of the compound or pharmaceutically-acceptable salt in a suitable liquid carrier(s), for example ethanol, glycerine, sorbitol, non-aqueous solvent such as polyethylene glycol, oils or water, optionally with a suspending agent, a solubilizing agent (such as a cyclodextrin), preservative, surfactant, wetting agent, flavoring or coloring agent. Alternatively, a liquid formulation can be prepared from a reconstitutable powder.

For example a powder containing active compound, suspending agent, sucrose and a sweetener can be reconstituted with water to form a suspension; a syrup can be prepared from a powder containing active ingredient, sucrose and a sweetener.

A composition in the form of a tablet can be prepared using any suitable pharmaceutical carrier(s) routinely used for preparing solid compositions. Examples of such carriers include magnesium stearate, starch, lactose, sucrose, microcrystalline cellulose and binders, for example polyvinylpyrrolidone. The tablet can also be provided with a color film coating, or color included as part of the carrier(s). In addition, active compound can be formulated in a controlled release dosage form as a tablet comprising a hydrophilic or hydrophobic matrix.

A composition in the form of a capsule can be prepared using routine encapsulation procedures, for example by incorporation of active compound and excipients into a hard gelatin capsule. Alternatively, a semi-solid matrix of active compound and high molecular weight polyethylene glycol can be prepared and filled into a hard gelatin capsule; or a solution of active compound in polyethylene glycol or a suspension in edible oil, for example liquid paraffin or fractionated coconut oil can be prepared and filled into a soft gelatin capsule.

Tablet binders that can be included are acacia, methylcellulose, sodium carboxymethylcellulose, poly-vinylpyrrolidone (Povidone), hydroxypropyl methylcellulose, sucrose, starch and ethylcellulose. Lubricants that can be used include magnesium stearate or other metallic stearates, stearic acid, silicone fluid, talc, waxes, oils and colloidal silica.

Flavoring agents such as peppermint, oil of wintergreen, cherry flavoring or the like can also be used. Additionally, it may be desirable to add a coloring agent to make the dosage form more attractive in appearance or to help identify the product.

The compounds of the invention and their pharmaceutically-acceptable salts that are active when given parenterally can be formulated for intramuscular, intrathecal, or intravenous administration.

A typical composition for intramuscular or intrathecal administration will consist of a suspension or solution of active ingredient in an oil, for example arachis oil or sesame oil. A typical composition for intravenous or intrathecal administration will consist of a sterile isotonic aqueous solution containing, for example active ingredient and dextrose or sodium chloride, or a mixture of dextrose and sodium chloride. Other examples are lactated Ringer's injection, lactated Ringer's plus dextrose injection, Normosol-M and dextrose, Isolyte E, acylated Ringer's injection, and the like. Optionally, a co-solvent, for example, polyethylene glycol; a chelating agent, for example, ethylenediamine tetraacetic acid; a solubilizing agent, for example, a cyclodextrin; and an antioxidant, for example, sodium metabisulphite, may be included in the formulation. Alternatively, the solution can be freeze dried and then reconstituted with a suitable solvent just prior to administration.

The compounds of this invention and their pharmaceutically-acceptable salts which are active on topical administration can be formulated as transdermal compositions or transdermal delivery devices ("patches"). Such compositions include, for example, a backing, active compound reservoir, a control membrane, liner and contact adhesive. Such transdermal patches may be used to provide continuous or discontinuous infusion of the compounds of the present invention in controlled amounts. The construction and use of transdermal patches for the delivery of pharmaceutical agents is well known in the art. See, for example, U.S. Pat. No. 5,023,252. Such patches may be constructed for continuous, pulsatile, or on demand delivery of pharmaceutical agents.

One preferred manner for administering a compound of the invention is inhalation. Inhalation is an effective means for delivering an agent directly to the respiratory tract. There are three general types of pharmaceutical inhalation devices: nebulizer inhalers, dry powder inhalers (DPI), and metered-dose inhalers (MDI). Conventional nebulizer devices produce a stream of high velocity air that causes a therapeutic agent to spray as a mist which is carried into the patient's respiratory tract. The therapeutic agent is formulated in a liquid form such as a solution or a suspension of micronized particles of respirable size, where micronized is typically defined as having about 90% or more of the particles with a diameter of less than about 10 µm.

A typical formulation for use in a conventional nebulizer device is an isotonic aqueous solution of a pharmaceutical salt of the active agent at a concentration of the active agent of between about 0.05 µg/mL and about 1 mg/mL. Suitable nebulizer devices are provided commercially, for example, by PARI GmbH (Stamberg, Germany). Other nebulizer devices have been disclosed, for example, in U.S. Pat. No. 6,123,068.

DPI's typically administer a therapeutic agent in the form of a free flowing powder that can be dispersed in a patient's air-stream during inspiration. Alternative DPI devices which use an external energy source to disperse the powder are also being developed. In order to achieve a free flowing powder, the therapeutic agent can be formulated with a suitable excipient (e.g., lactose or starch). A dry powder formulation can be made, for example, by combining dry lactose particles with micronized particles of a suitable form, typically a pharmaceutically-acceptable salt, of a compound of the invention (i.e. the active agent) and dry blending. Alternatively, the agent can be formulated without excipients. The formulation is loaded into a dry powder dispenser, or into inhalation cartridges or capsules for use with a dry powder delivery device.

Examples of DPI delivery devices provided commercially include Diskhaler (GlaxoSmithKline, Research Triangle Park, N.C.) (see, e.g., U.S. Pat. No. 5,035,237); Diskus (GlaxoSmithKline) (see, e.g., U.S. Pat. No. 6,378,519; Turbuhaler (AstraZeneca, Wilmington, Del.) (see, e.g., U.S. Pat. No. 4,524,769); and Rotahaler (GlaxoSmithKline) (see, e.g., U.S. Pat. No. 4,353,365). Further examples of suitable DPI devices are described in U.S. Pat. Nos. 5,415,162, 5,239,993, and 5,715,810 and references therein.

MDI's typically discharge a measured amount of therapeutic agent using compressed propellant gas. Formulations for MDI administration include a solution or suspension of active ingredient in a liquefied propellant. While chlorofluorocarbons, such as $CCl_3F$, conventionally have been used as propellants, due to concerns regarding adverse affects of such agents on the ozone layer, formulations using hydrofluoroalklanes (HFA), such as 1,1,1,2-tetrafluoroethane (HFA 134a) and 1,1,1,2,3,3,3,-heptafluoro-n-propane, (HFA 227) have been developed. Additional components of HFA formulations for MDI administration include co-solvents, such as ethanol or pentane, and surfactants, such as sorbitan trioleate, oleic acid, lecithin, and glycerin. (See, for example, U.S. Pat. No. 5,225,183, EP 0717987 A2, and WO 92/22286.)

Thus, a suitable formulation for MDI administration can include from about 0.001% to about 2% by weight of the present crystalline form, from about 0% to about 20% by weight ethanol, and from about 0% to about 5% by weight surfactant, with the remainder being the HFA propellant. In one approach, to prepare the formulation, chilled or pressurized hydrofluoroalkane is added to a vial containing the present crystalline form, ethanol (if present) and the surfactant (if present). To prepare a suspension, the pharmaceutical salt is provided as micronized particles. The formulation is loaded into an aerosol canister, which forms a portion of an MDI device. Examples of MDI devices developed specifically for use with HFA propellants are provided in U.S. Pat. Nos. 6,006,745 and 6,143,227.

In an alternative preparation, a suspension formulation is prepared by spray drying a coating of surfactant on micronized particles of a pharmaceutical salt of active compound. (See, for example, WO 99/53901 and WO 00/61108. ) For additional examples of processes of preparing respirable particles, and formulations and devices suitable for inhalation dosing see U.S. Pat. Nos. 6,268,533, 5,983,956, 5,874,063, and 6,221,398, and WO 99/55319 and WO 00/30614.

It will be understood that any form of the compounds of the invention, (i.e. free base, pharmaceutical salt, or solvate) that is suitable for the particular mode of administration, can be used in the pharmaceutical compositions discussed above.

The active compounds are useful as $\beta_2$ adrenergic receptor agonists and therefore are useful for treating medical diseases or conditions mediated by $\beta_2$ adrenergic receptors or associated with $\beta_2$ adrenergic receptor activity in a mammal, i.e. medical conditions which are ameliorated by treatment with a $\beta_2$ adrenergic receptor agonist. Such medical conditions include but are not limited to a pulmonary disease, such as asthma or chronic obstructive pulmonary disease, pre-term labor, a neurological disorder, a cardiac disorder, or inflammation.

The active compounds are effective over a wide dosage range and are generally administered in a therapeutically effective amount. It will be understood, however, that the amount of the compound actually administered will be determined by a physician, in the light of the relevant circumstances, including the condition to be treated, the chosen route of administration, the actual compound administered and its relative activity, the age, weight, and response of the individual patient, the severity of the patient's symptoms, and the like.

Suitable doses of the therapeutic agents for inhalation administration are in the general range of from about 0.05 µg/day to about 1000 µg/day, preferably from about 0.1 µg/day to about 500 µg/day. It will be understood that the fraction of active agent delivered to the lung characteristic of particular delivery devices is taken into account in determining suitable doses for inhalation administration.

A compound can be administered in a periodic dose: weekly, multiple times per week, daily, or multiple doses per day. The treatment regimen may require administration over extended periods of time, for example, for several weeks or months, or the treatment regimen may require chronic administration. Suitable doses for oral administration are in the general range of from about 0.05 µg/day to about 100 mg/day, preferably 0.5 to 1000 µg/day.

Among other properties, compounds of the invention have been found to be potent and selective agonists of the $\beta_2$ adrenergic receptor. In particular, compounds of the invention demonstrate excellent selectivity for the $\beta_2$ adrenergic receptor as compared with the $\beta_1$ and $\beta_3$ adrenergic receptors. Furthermore, compounds of the invention have been found to possess surprising and unexpected duration of action. As described in the biological assays below, compounds of the invention demonstrated duration of action greater than 24 hours in an animal model of bronchoprotection.

The invention thus provides a method of treating a disease or condition in a mammal associated with $\beta_2$ adrenergic receptor activity comprising administering to the mammal a therapeutically effective amount of a compound of the invention or of a pharmaceutical composition comprising a compound of the invention.

The present active agents can also be co-administered with one or more other therapeutic agents. For example, the present agents can be administered in combination with one or more therapeutic agents selected from anti-inflammatory agents (e.g. corticosteroids and non-steroidal anti-inflammatory agents (NSAIDs), antichlolinergic agents (particularly muscarinic receptor antagonists), other $\beta_2$ adrenergic receptor agonists, antiinfective agents (e.g. antibiotics or antivirals) or antihistamines. The invention thus provides, in a further aspect, a combination comprising a compound of the invention together with one or more therapeutic agent, for example, an anti-inflammatory agent, an antichlolinergic agent, another $\beta_2$ adrenergic receptor agonist, an antiinfective agent or an antihistamine.

The other therapeutic agents can be used in the form of pharmaceutically-acceptable salts or solvates. As appropriate, the other therapeutic agents can be used as optically pure stereoisomers.

Suitable anti-inflammatory agents include corticosteroids and NSAIDs. Suitable corticosteroids which may be used in combination with the compounds of the invention are those oral and inhaled corticosteroids and their pro-drugs which have anti-inflammatory activity. Examples include methyl prednisolone, prednisolone, dexamethasone, fluticasone propionate, 6α,9α-difluoro-17α-[(2-furanylcarbonyl)oxy]-11β-hydroxy-16α-methyl-3-oxo-androsta-1,4-diene-17β-carbothioic acid S-fluoromethyl ester, 6α,9α-difluoro-11β-hydroxy-16α-methyl-3-oxo-17α-propionyloxy-androsta-1,4-diene-17β-carbothioic acid S-(2-oxo-tetrahydro-furan-3S-yl) ester, beclomethasone esters (e.g. the 17-propionate ester or the 17,21-dipropionate ester), budesonide, flunisolide, mometasone esters (e.g. the furoate ester), triamcinolone acetonide, rofleponide, ciclesonide, butixocort propionate, RPR-106541, and ST-126. Preferred corticosteroids include fluticasone propionate, 6α,9α-difluoro-11β-hydroxy-16α-methyl-17α-[(4-methyl-1,3-thiazole-5-carbonyl)oxy]-3-oxo-androsta-1,4-diene-17β-carbothioic acid S-fluoromethyl ester and 6α,9α-difluoro-17α-[(2-furanylcarbonyl)oxy]-11β-hydroxy-16α-methyl-3-oxo-androsta-1,4-diene-17β-carbothioic acid S-fluoromethyl ester, more preferably 6α,9α-difluoro-17α-[(2-furanylcarbonyl)oxy]-11β-hydroxy-16α-methyl-3-oxo-androsta-1,4-diene-17β-carbothioic acid S-fluoromethyl ester.

Suitable NSAIDs include sodium cromoglycate; nedocromil sodium; phosphodiesterase (PDE) inhibitors (e.g. theophylline, PDE4 inhibitors or mixed PDE3/PDE4 inhibitors); leukotriene antagonists (e.g. monteleukast); inhibitors of leukotriene synthesis; iNOS inhibitors; protease inhibitors, such as tryptase and elastase inhibitors; beta-2 integrin antagonists and adenosine receptor agonists or antagonists (e.g. adenosine 2a agonists); cytokine antagonists (e.g. chemokine antagonists such as, an interleukin antibody (αIL antibody), specifically, an αIL-4 therapy, an αIL-13 therapy, or a combination thereof); or inhibitors of cytokine synthesis. Suitable other $\beta_2$-adrenoreceptor agonists include salmeterol (e.g. as the xinafoate), salbutamol (e.g. as the sulphate or the free base), formoterol (e.g. as the fumarate), fenoterol or terbutaline and salts thereof.

Also of interest is use of the present active agent in combination with a phosphodiesterase 4 (PDE4) inhibitor or a mixed PDE3/PDE4 inhibitor. Representative phosphodiesterase-4 (PDE4) inhibitors or mixed PDE3/PDE4 inhibitors include, but are not limited to cis 4-cyano-4-(3-cyclopentyloxy-4-methoxyphenyl)cyclohexan-1-carboxylic acid, 2-carbomethoxy-4-cyano-4-(3-cyclopropylmethoxy-4-difluoromethoxyphenyl)cyclohexan-1-one; cis-[4-cyano-4-(3-cyclopropylmethoxy-4-difluoromethoxyphenyl) cyclohexan-1-ol]; cis-4-cyano-4-[3-(cyclopentyloxy)-4-methoxyphenyl]cyclohexane-1-carboxylic acid and the like, or pharmaceutically-acceptable salts thereof. Other representative PDE4 or mixed PDE4/PDE3 inhibitors include AWD-12-281 (elbion); NCS-613 (INSERM); D-4418 (Chiroscience and Schering-Plough); CI-1018 or PD-168787 (Pfizer); benzodioxole compounds disclosed in WO99/16766 (Kyowa Hakko); K-34 (Kyowa Hakko); V-11294A (Napp); roflumilast (Byk-Gulden); pthalazinone compounds disclosed in WO99/47505 (Byk-Gulden); Pumafentrine (Byk-Gulden, now Altana); arofylline (Almirall-Prodesfarma); VM554/UM565 (Vernalis); T-440 (Tanabe Seiyaku); and T2585 (Tanabe Seiyaku).

Suitable anticholinergic agents are those compounds that act as antagonists at the muscarinic receptor, in particular those compounds which are antagonists of the $M_1$, $M_2$, or $M_3$ receptors, or of combinations thereof. Exemplary compounds include the alkaloids of the belladonna plants as illustrated by the likes of atropine, scopolamine, homatropine, hyoscyamine; these compounds are normally administered as a salt, being tertiary amines. These drugs, particularly the salt forms, are readily available from a number of commercial sources or can be made or prepared from literature data via, to wit:

Atropine—CAS-51-55-8 or CAS-51-48-1 (anhydrous form), atropine sulfate—CAS-5908-99-6; atropine oxide—CAS-4438-22-6 or its HCl salt—CAS-4574-60-1 and methylatropine nitrate—CAS-52-88-0.

Homatropine—CAS-87-00-3, hydrobromide salt—CAS-51-56-9, methylbromide salt—CAS-80-49-9.

Hyoscyamine (d, 1)—CAS-101-31-5, hydrobromide salt—CAS-306-03-6 and sulfate salt—CAS-6835-16-1.

Scopolamine—CAS-51-34-3, hydrobromide salt—CAS-6533-68-2, methylbromide salt—CAS-155-41-9.

Preferred anticholinergics include ipratropium (e.g. as the bromide), sold under the name Atrovent, oxitropium (e.g. as the bromide) and tiotropium (e.g. as the bromide) (CAS-139404-48-1). Also of interest are: methantheline (CAS-53-46-3), propantheline bromide (CAS-50-34-9), anisotropine methyl bromide or Valpin 50 (CAS-80-50-2), clidinium bromide (Quarzan, CAS-3485-62-9), copyrrolate (Robinul), isopropamide iodide (CAS-71-81-8), mepenzolate bromide (U.S. Pat. No. 2,918,408), tridihexethyl chloride (Pathilone, CAS-4310-35-4), and hexocyclium methylsulfate (Tral, CAS-1 15-63-9). See also cyclopentolate hydrochloride (CAS-5870-29-1), tropicamide (CAS-1508-75-4), trihexyphenidyl hydrochloride (CAS-144-11-6), pirenzepine (CAS-29868-97-1), telenzepine (CAS-80880-90-9), AF-DX 116, or methoctramine, and the compounds disclosed in WO01/04118, the disclosure of which is hereby incorporated by reference.

Suitable antihistamines (also referred to as $H_1$-receptor antagonists) include any one or more of the numerous antagonists known which inhibit $H_1$-receptors, and are safe for human use. All are reversible, competitive inhibitors of the interaction of histamine with $H_1$-receptors. The majority of these inhibitors, mostly first generation antagonists, are characterized, based on their core structures, as ethanolamines, ethylenediamines, and alkylamines. In addition, other first generation antihistamines include those which can be characterized as based on piperizine and phenothiazines. Second generation antagonists, which are non-sedating, have a similar structure-activity relationship in that they retain the core ethylene group (the alkylamines) or mimic a tertiary amine group with piperizine or piperidine. Exemplary antagonists are as follows:

Ethanolamines: carbinoxamine maleate, clemastine fumarate, diphenylhydramine hydrochloride, and dimenhydrinate.

Ethylenediamines: pyrilamine amleate, tripelennamine HCl, and tripelennamine citrate.

Alkylamines: chlorpheniramine and its salts such as the maleate salt, and acrivastine.

Piperazines: hydroxyzine HCl, hydroxyzine pamoate, cyclizine HCl, cyclizine lactate, meclizine HCl, and cetirizine HCl.

Piperidines: Astemizole, levocabastine HCl, loratadine or its descarboethoxy analogue, and terfenadine and fexofenadine hydrochloride or another pharmaceutically-acceptable salt.

Azelastine hydrochloride is yet another $H_1$ receptor antagonist which may be used in combination with a compound of the invention.

Examples of preferred anti-histamines include methapyrilene and loratadine.

The invention thus provides, in a further aspect, a combination comprising a compound of formula (I) or a pharmaceutically-acceptable salt or solvate or stereoisomer thereof and a corticosteroid. In particular, the invention provides a combination wherein the corticosteroid is fluticasone propionate or wherein the corticosteroid is 6α,9α-difluoro-17α-[(2-furanylcarbonyl)oxy]-11β-hydroxy-16α-methyl-3-oxo-androsta-1,4-diene-17β-carbothioic acid S-fluoromethyl ester or 6α,9α-difluoro-11β-hydroxy-16α-methyl-3-oxo-17α-propionyloxy-androsta-1,4-diene-17β-carbothioic acid S-(2-oxo-tetrahydro-furan-3S-yl) ester.

The invention thus provides, in a further aspect, a combination comprising a compound of formula (I) or a pharmaceutically-acceptable salt or solvate or stereoisomer thereof and a PDE4 inhibitor.

The invention thus provides, in a further aspect, a combination comprising a compound of formula (I) or a pharmaceutically-acceptable salt or solvate or stereoisomer thereof and an anticholinergic agent.

The invention thus provides, in a further aspect, a combination comprising a compound of formula (I) or a pharmaceutically-acceptable salt or solvate or stereoisomer thereof and an antihistamine.

The invention thus provides, in a further aspect, a combination comprising a compound of formula (I) or a pharmaceutically-acceptable salt or solvate or stereoisomer thereof together with a PDE4 inhibitor and a corticosteroid.

The invention thus provides, in a further aspect, a combination comprising a compound of formula (I) or a pharmaceutically-acceptable salt or solvate or stereoisomer thereof together with an anticholinergic agent and a corticosteroid.

As used in the above combinations, the term, "a compound of formula (I)" includes a compound of formula (II) and preferred groups thereof, and any individually disclosed compound or compounds.

Accordingly, the pharmaceutical compositions of the invention can optionally comprise combinations of a compound of formula (I) or a pharmaceutically-acceptable salt or solvate or stereoisomer thereof with one or more other therapeutic agents, as described above.

The individual compounds of such combinations may be administered either sequentially or simultaneously in separate or combined pharmaceutical formulations. Appropriate doses of known therapeutic agents will be readily appreciated by those skilled in the art. Methods of treatment of the invention, therefore, include administration of the individual compounds of such combinations either sequentially or simultaneously in separate or combined pharmaceutical formulations.

Thus, according to a further aspect, the invention provides a method of treating a disease or condition associated with $β_2$ adrenergic receptor activity in a mammal, comprising administering to the mammal a therapeutically effective amount of a combination of a compound of formula (I) or a pharmaceutically-acceptable salt or solvate or stereoisomer thereof with one or more other therapeutic agents.

Since compounds of the invention are $β_2$ adrenergic receptor agonists, such compounds are also useful as research tools for investigating or studying biological systems or samples having $β_2$ adrenergic receptors, or for discovering new $β_2$ adrenergic receptor agonists. Moreover, since compounds of the invention exhibit selectivity for $β_2$ adrenergic receptors as compared with binding and functional activity at receptors of other β adrenergic subtypes, such compounds are also useful for studying the effects of selective agonism of $β_2$ adrenergic receptors in a biological system or sample. Any suitable biological system or sample having $β_2$ adrenergic receptors may be employed in such studies which may be conducted either in vitro or in vivo.

Representative biological systems or samples suitable for such studies include, but are not limited to, cells, cellular extracts, plasma membranes, tissue samples, mammals (such as mice, rats, guinea pigs, rabbits, dogs, pigs, etc.) and the like. The effects of agonizing the $β_2$ adrenergic receptor are determined using conventional procedures and equipment, such as radioligand binding assays and functional assays, for example the assay for ligand-mediated changes in intracellular cyclic adenosine monophosphate (cAMP) described below, or assays of a similar nature. A $β_2$ adrenergic receptor-agonizing amount of a compound of the invention will typically range from about 1 nanomolar to about 1000 nanomolar. When compounds of the invention are used as research tools for discovering new $β_2$ adrenergic receptor agonists, the invention also includes, as separate embodiments, both the generation of comparison data (using the appropriate assays) and the analysis of the test data to identify test compounds of interest.

The following non-limiting examples illustrate representative pharmaceutical compositions of the invention. Additional suitable carriers for formulations of the active compounds of the present invention can also be found in Remington: *The Science and Practice of Pharmacy*, 20th Edition, Lippincott Williams & Wilkins, Philadelphia, Pa., 2000.

FORMULATION EXAMPLE A

This example illustrates the preparation of a representative pharmaceutical composition for oral administration of a compound of this invention:

| Ingredients | Quantity per tablet, (mg) |
| --- | --- |
| Active Compound | 1 |
| Lactose, spray-dried | 148 |
| Magnesium stearate | 2 |

The above ingredients are mixed and introduced into a hard-shell gelatin capsule.

FORMULATION EXAMPLE B

This example illustrates the preparation of another representative pharmaceutical composition for oral administration of a compound of this invention:

| Ingredients | Quantity per tablet, (mg) |
| --- | --- |
| Active Compound | 1 |
| Cornstarch | 50 |
| Lactose | 145 |
| Magnesium stearate | 5 |

The above ingredients are mixed intimately and pressed into single scored tablets.

FORMULATION EXAMPLE C

This example illustrates the preparation of a representative pharmaceutical composition for oral administration of a compound of this invention.

An oral suspension is prepared having the following composition.

| Ingredients | |
| --- | --- |
| Active Compound | 3 mg |
| Fumaric acid | 0.5 g |
| Sodium chloride | 2.0 g |
| Methyl paraben | 0.1 g |
| Granulated sugar | 25.5 g |
| Sorbitol (70% solution) | 12.85 g |
| Veegum K (Vanderbilt Co.) | 1.0 g |
| Flavoring | 0.035 mL |
| Colorings | 0.5 mg |
| Distilled water | q.s. to 100 mL |

FORMULATION EXAMPLE D

This example illustrates the preparation of a representative pharmaceutical composition containing a compound of this invention.

An injectable preparation buffered to a pH of 4 is prepared having the following composition:

| Ingredients | |
| --- | --- |
| Active Compound | 0.1 mg |
| Sodium Acetate Buffer Solution (0.4 M) | 2.0 mL |
| HCl (1N) | q.s. to pH 4 |
| Water (distilled, sterile) | q.s. to 20 mL |

FORMULATION EXAMPLE E

This example illustrates the preparation of a representative pharmaceutical composition for injection of a compound of this invention.

A reconstituted solution is prepared by adding 20 mL of sterile water to 1 mg of the compound of this invention. Before use, the solution is then diluted with 200 mL of an intravenous fluid that is compatible with the active compound. Such fluids are chosen from 5% dextrose solution, 0.9% sodium chloride, or a mixture of 5% dextrose and 0.9% sodium chloride. Other examples are lactated Ringer's injection, lactated Ringer's plus 5% dextrose injection, Normosol-M and 5% dextrose, Isolyte E, and acylated Ringer's injection.

FORMULATION EXAMPLE F

This example illustrates the preparation of a representative pharmaceutical composition for topical application of a compound of this invention.

| Ingredients | grams |
| --- | --- |
| Active compound | 0.2-10 |
| Span 60 | 2 |
| Tween 60 | 2 |
| Mineral oil | 5 |
| Petrolatum | 10 |
| Methyl paraben | 0.15 |
| Propyl paraben | 0.05 |
| BHA (butylated hydroxy anisole) | 0.01 |
| Water | q.s. to 100 |

All of the above ingredients, except water, are combined and heated to 60° C. with stirring. A sufficient quantity of water at 60° C. is then added with vigorous stirring to emulsify the ingredients, and water then added q.s. 100 g.

FORMULATION EXAMPLE G

This example illustrates the preparation of a representative pharmaceutical composition containing a compound of the invention.

An aqueous aerosol formulation for use in a nebulizer is prepared by dissolving 0.1 mg of a pharmaceutical salt of active compound in a 0.9% sodium chloride solution acidified with citric acid. The mixture is stirred and sonicated until the active salt is dissolved. The pH of the solution is adjusted to a value in the range of from 3 to 8 by the slow addition of NaOH.

FORMULATION EXAMPLE H

This example illustrates the preparation of a dry powder formulation containing a compound of the invention for use in inhalation cartridges.

Gelatin inhalation cartridges are filled with a pharmaceutical composition having the following ingredients:

| Ingredients | mg/cartridge |
|---|---|
| Pharmaceutical salt of active compound | 0.2 |
| Lactose | 25 |

The pharmaceutical salt of active compound is micronized prior to blending with lactose. The contents of the cartridges are administered using a powder inhaler.

FORMULATION EXAMPLE I

This example illustrates the preparation of a dry powder formulation containing a compound of the invention for use in a dry powder inhalation device.

A pharmaceutical composition is prepared having a bulk formulation ratio of micronized pharmaceutical salt to lactose of 1:200. The composition is packed into a dry powder inhalation device capable of delivering between about 10 µg and about 100 µg of active drug ingredient per dose.

FORMULATION EXAMPLE J

This example illustrates the preparation of a formulation containing a compound of the invention for use in a metered dose inhaler.

A suspension containing 5% pharmaceutical salt of active compound, 0.5% lecithin, and 0.5% trehalose is prepared by dispersing 5 g of active compound as micronized particles with mean size less than 10 µm in a colloidal solution formed from 0.5 g of trehalose and 0.5 g of lecithin dissolved in 100 mL of demineralized water. The suspension is spray dried and the resulting material is micronized to particles having a mean diameter less than 1.5 µm. The particles are loaded into canisters with pressurized 1,1,1,2-tetrafluoroethane.

FORMULATION EXAMPLE K

This example illustrates the preparation of a formulation containing a compound of the invention for use in a metered dose inhaler.

A suspension containing 5% pharmaceutical salt of active compound and 0.1% lecithin is prepared by dispersing 10 g of active compound as micronized particles with mean size less than 10 µm in a solution formed from 0.2 g of lecithin dissolved in 200 mL of demineralized water. The suspension is spray dried and the resulting material is micronized to particles having a mean diameter less than 1.5 µm. The particles are loaded into canisters with pressurized 1,1,1,2,3,3,3-heptafluoro-n-propane.

Biological Assays

The compounds of this invention, and their pharmaceutically-acceptable salts, exhibit biological activity and are useful for medical treatment. The ability of a compound to bind to the $\beta_2$ adrenergic receptor, as well as its selectivity, agonist potency, and intrinsic activity can be demonstrated using Tests A-B below, or can be demonstrated using other tests that are known in the art.

| Abbreviations | |
|---|---|
| % Eff | % efficacy |
| ATCC | American Type Culture Collection |
| BSA | Bovine Serum Albumin |
| cAMP | Adenosine 3':5'-cyclic monophosphate |
| DMEM | Dulbecco's Modified Eagle's Medium |
| DMSO | Dimethyl sulfoxide |
| EDTA | Ethylenediaminetetraacetic acid |
| Emax | maximal efficacy |
| FBS | Fetal bovine serum |
| Gly | Glycine |
| HEK-293 | Human embryonic kidney —293 |
| PBS | Phosphate buffered saline |
| rpm | rotations per minute |
| Tris | Tris(hydroxymethyl)aminomethane |

Membrane Preparation from Cells Expressing Human $\beta_1$ or $\beta_2$ Adrenergic Receptors HEK-293 derived cell lines stably expressing cloned human $\beta_1$ or $\beta_2$ adrenergic receptors, respectively, were grown to near confluency in DMEM with 10% dialyzed FBS in the presence of 500 µg/mL Geneticin. The cell monolayer was lifted with Versene 1:5,000 (0.2 g/L EDTA in PBS) using a cell scraper. Cells were pelleted by centrifugation at 1,000 rpm, and cell pellets were either stored frozen at −80° C. or membranes were prepared immediately. For preparation, cell pellets were resuspended in lysis buffer (10 mM Tris/HCL pH 7.4 @ 4° C., one tablet of "Complete Protease Inhibitor Cocktail Tablets with 2 mM EDTA" per 50 mL buffer (Roche cat.# 1697498, Roche Molecular Biochemicals, Indianapolis, Ind.)) and homogenized using a tight-fitting Dounce glass homogenizer (20 strokes) on ice. The homogenate was centrifuged at 20,000×g, the pellet was washed once with lysis buffer by resuspension and centrifugation as above. The final pellet was resuspended in membrane buffer (75 mM Tris/HCl pH 7.4, 12.5 mM $MgCl_2$, 1 mM EDTA @ 25° C.). Protein concentration of the membrane suspension was determined by the method of Bradford (Bradford M M., *Analytical Biochemistry*, 1976, 72, 248-54). Membranes were stored frozen in aliquots at −80° C.

Test A

Radioligand Binding Assay on Human $\beta_1$ and $\beta_2$ Adrenergic Receptors

Binding assays were performed in 96-well microtiter plates in a total assay volume of 100 µL with 5 µg membrane protein for membranes containing the human $\beta_2$ adrenergic receptor, or 2.5 µg membrane protein for membranes containing the human $\beta_1$ adrenergic receptor in assay buffer (75 mM Tris/HCl pH 7.4 @ 25° C., 12.5 mM $MgCl_2$, 1 mM EDTA, 0.2% BSA). Saturation binding studies for determination of $K_d$ values of the radioligand were done using [$^3$H]dihydroalprenolol (NET-720, 100 Ci/mmol, PerkinElmer Life Sciences Inc., Boston, Mass.) at 10 different concentrations ranging from 0.01 nM-200 nM. Displacement assays for determination of $pK_i$ values of compounds were done with [$^3$H]dihydroalprenolol at 1 nM and 10 different concentrations of compound ranging from 40 µM-10 µM. Compounds were dissolved to a concentration of 10 mM in dissolving buffer (25 mM Gly-HCl pH 3.0 with 50% DMSO), then diluted to 1 mM in 50 mM Gly-HCl pH 3.0, and from there serially diluted into assay buffer. Non-specific binding was determined in the presence of 10 μM unlabeled alprenolol. Assays were incubated for 90 minutes at room temperature, binding reactions were terminated by rapid filtration over GF/B glass fiber filter plates (Packard BioScience Co., Meriden, Conn.) presoaked in 0.3% polyethyleneimine. Filter plates were washed three times with filtration buffer (75 mM Tris/HCl pH 7.4 @ 4° C., 12.5 mM $MgCl_2$, 1 mM EDTA) to remove unbound radioactivity. Plates were dried, 50 lL Microscint-20 liquid scintillation fluid (Packard BioScience Co., Meriden, Conn.) was added and plates were counted in a Packard Topcount liquid scintillation counter (Packard BioScience Co., Meriden, Conn.). Binding data were analyzed by nonlinear regression analysis with the GraphPad Prism Software package (GraphPad Software, Inc., San Diego, Calif.) using the 3-parameter model for one-site competition. The curve minimum was fixed to the value for nonspecific binding, as determined in the presence of 10 μM alprenolol. $K_i$ values for compounds were calculated from observed $IC_{50}$ values and the $K_d$ value of the radioligand using the Cheng-Prusoff equation (Cheng Y, and Prusoff W H., *Biochemical Pharmacology*, 1973, 22, 23, 3099-108). The receptor subtype selectivity was calculated as the ratio of $K_i(\beta_1)/K_i(\beta_2)$. Compounds of the invention demonstrated greater binding at the $\beta_2$ adrenergic receptor than at the $\beta_1$ adrenergic receptor, i.e. $K_i(\beta_1) > K_i(\beta_2)$ with selectivity greater than about 100.

Test B

Whole-cell cAMP Flashplate Assays with Cell Lines Heterologously Expressing Human $\beta_1$ Adrenoceptor, $\beta_2$ Adrenoceptor, and $\beta_3$ Adrenoceptor, Respectively A HEK-293 cell line stably expressing cloned human $\beta_1$ adrenergic receptor (clone H34.1) was grown to about 70%-90% confluency in medium consisting of DMEM supplemented with 10% FBS and 500 μg/mL Geneticin. A HEK-293 cell line stably expressing cloned human $\alpha_2$-adrenoceptor (clone H24.14) was grown in the same medium to full confluency. A CHO-K1 cell line stably expressing cloned human $\beta_3$-adrenoceptor was grown to about 70%-90% confluency in Ham's F-12 medium supplemented with 10% FBS and with 800 μg/mL Geneticin added to every fifth passage. The day before the assay, cultures were switched to the same growth-media without antibiotics.

cAMP assays were performed in a radioimmunoassay format using the Flashplate Adenylyl Cyclase Activation Assay System with $^{125}$I-cAMP (NEN SMP004, PerkinElmer Life Sciences Inc., Boston, Mass.), according to the manufacturers instructions.

On the day of the assay, cells were rinsed once with PBS, lifted with Versene 1:5,000 (0.2 g/L EDTA in PBS) and counted. Cells were pelleted by centrifugation at 1,000 rpm and resuspended in stimulation buffer prewarmed to 37° C. For cells expressing the $\beta_1$-adrenoceptor, 10 nM ICI 118,551 were added to the stimulation buffer, and cells were incubated for 10 min at 37° C. Cells were used at final concentrations of 30,000, 40,000 and 70,000 cells/well for the $\beta_1$-adrenoceptor-, the $\beta_2$-adrenoceptor- and the $\beta_3$-adrenoceptor expressing cells, respectively. Compounds were dissolved to a concentration of 10 mM in DMSO, then diluted to 1 mM in 50 mM Gly-HCl pH 3.0, and from there serially diluted into assay buffer (75 mM Tris/HCl pH 7.4 @ 25° C., 12.5 mM $MgCl_2$, 1 mM EDTA, 0.2% BSA). Compounds were tested in the assay at 11 different concentrations, ranging from 10 μM to 9.5 pM. Reactions were incubated for 10 min at 37° C. and stopped by addition of 100 μl ice-cold detection buffer. Plates were sealed, incubated over night at 4° C. and counted the next morning in a topcount scintillation counter (Packard BioScience Co., Meriden, Conn.). The amount of cAMP produced per mL of reaction was calculated based on the counts observed for the samples and cAMP standards, as described in the manufacturer's user manual. Data were analyzed by nonlinear regression analysis with the GraphPad Prism Software package (GraphPad Software, Inc., San Diego, Calif.) using the 3-parameter model for sigmoidal dose-response (Hill slope=1). Agonist potencies were expressed as $pEC_{50}$ values.

Compounds of the invention demonstrated potent activity at the $\beta_2$ adrenergic receptor in this assay, as evidenced by $pEC_{50}$ values greater than about 8.5. In addition, the compounds tested demonstrated selectivity in functional activity at the $\beta_2$ receptor as compared with functional activity at the $\beta_1$ and $\beta_3$ receptors. In particular, compounds of the invention demonstrated $EC_{50}(\beta_1)/EC_{50}(\beta_2)$ ratios of greater than about 50 and $EC_{50}(\beta_3)/EC_{50}(\beta_2)$ ratios of greater than about 600.

Test C

Whole-cell cAMP Flashplate Assay with a Lung Epithelial Cell Line Endogenously Expressing Human $\beta_2$ Adrenergic Receptor For the determination of agonist potencies and efficacies (intrinsic activities) in a cell line expressing endogenous levels of $\beta_2$ adrenergic receptor, a human lung epithelial cell line (BEAS-2B) was used (ATCC CRL-9609, American Type Culture Collection, Manassas, Va.) (January B, et al., *British Journal of Pharmacology*, 1998, 123, 4, 701-11). Cells were grown to 75-90% confluency in complete, serum-free medium (LHC-9 MEDIUM containing Epinephrine and Retinoic Acid, cat # 181-500, Biosource International, Camarillo, Calif.). The day before the assay, medium was switched to LHC-8 (No epinephrine or retinoic acid, cat # 141-500, Biosource International, Camarillo, Calif.).

cAMP assays were performed in a radioimmunoassay format using the Flashplate Adenylyl Cyclase Activation Assay System with $^{125}$I-cAMP (NEN SMP004, PerkinElmer Life Sciences Inc., Boston, Mass.), according to the manufacturers instructions.

On the day of the assay, cells were rinsed with PBS, lifted by scraping with 5 mM EDTA in PBS, and counted. Cells were pelleted by centrifugation at 1,000 rpm and resuspended in stimulation buffer prewarmed to 37° C. at a final concentration of 600,000 cells/mL. Cells were used at a final concentration of 30,000 cells/well in the assay. Compounds were dissolved to a concentration of 10 mM in dissolving buffer (25 mM Gly-HCl pH 3.0 with 50% DMSO), then diluted to 1 mM in 50 mM Gly-HCl pH 3.0, and from there serially diluted into assay buffer (75 mM Tris/HCl pH 7.4 @ 25° C., 12.5 mM $MgCl_2$, 1 mM EDTA, 0.2% BSA).

Compounds were tested in the assay at 10 different concentrations, ranging from 10 μM to 40 pM. Maximal response was determined in the presence of 10 μM Isoproterenol. Reactions were incubated for 10 min at 37° C. and stopped by addition of 100 μl ice-cold detection buffer. Plates were sealed, incubated over night at 4° C. and counted the next morning in a topcount scintillation counter (Packard BioScience Co., Meriden, Conn.). The amount of cAMP produced per mL of reaction was calculated based on the counts observed for samples and cAMP standards, as described in the manufacturer's user manual. Data were analyzed by nonlinear regression analysis with the GraphPad Prism Software package (GraphPad Software, Inc., San Diego, Calif.) using the 4-parameter model for sigmoidal dose-response with variable slope. Compounds of the invention tested in this assay demonstrated $pEC_{50}$ values greater than about 8.

Compound efficacy (% Eff) was calculated from the ratio of the observed Emax (TOP of the fitted curve) and the maximal response obtained for 10 μM isoproterenol and was expressed as % Eff relative to isoproterenol. The compounds tested demonstrated a % Eff greater than about 50.

Test D

Assay of Bronchoprotection Against Acetylcholine-Induced Bronchospasm in a Guinea Pig Model Groups of 6 male guinea pigs (Duncan-Hartley (HsdPoc: DH) Harlan, Madison, Wis.) weighing between 250 and 350 g were individually identified by cage cards. Throughout the study animals were allowed access to food and water ad libitum.

Test compounds were administered via inhalation over 10 minutes in a whole-body exposure dosing chamber (R&S Molds, San Carlos, Calif.). The dosing chambers were arranged so that an aerosol was simultaneously delivered to 6 individual chambers from a central manifold. Following a 60 minute acclimation period and a 10 minute exposure to nebulized water for injection (WFI), guinea pigs were exposed to an aerosol of test compound or vehicle (WFI). These aerosols were generated from aqueous solutions using an LC Star Nebulizer Set (Model 22F51, PARI Respiratory Equipment, Inc. Midlothian, Va.) driven by a mixture of gases ($CO_2$=5%, $O_2$=21% and $N_2$=74%) at a pressure of 22 psi. The gas flow through the nebulizer at this operating pressure was approximately 3 L/minute. The generated aerosols were driven into the chambers by positive pressure. No dilution air was used during the delivery of aerosolized solutions. During the 10 minute nebulization, approximately 1.8 mL of solution was nebulized. This was measured gravimetrically by comparing pre- and post-nebulization weights of the filled nebulizer.

The bronchoprotective effects of compounds administered via inhalation were evaluated using whole body plethysmography at 1.5, 24, 48 and 72 hours post-dose. Forty-five minutes prior to the start of the pulmonary evaluation, each guinea pig was anesthetized with an intramuscular injection of ketamine (43.75 mg/kg), xylazine (3.50 mg/kg) and acepromazine (1.05 mg/kg). After the surgical site was shaved and cleaned with 70% alcohol, a 2-5 cm midline incision of the ventral aspect of the neck was made. Then, the jugular vein was isolated and cannulated with a saline-filled polyethylene catheter (PE-50, Becton Dickinson, Sparks, Md.) to allow for intravenous infusions of a 0.1 mg/mL solution of acetylcholine (Ach), (Sigma-Aldrich, St. Louis, Mo.) in saline. The trachea was then dissected free and cannulated with a 14 G teflon tube (#NE-014, Small Parts, Miami Lakes, Fla.). If required, anesthesia was maintained by additional intramuscular injections of the aforementioned anesthetic cocktail. The depth of anesthesia was monitored and adjusted if the animal responded to pinching of its paw or if the respiration rate was greater than 100 breaths/minute.

Once the cannulations were complete, the animal was placed into a plethysmograph (#PLY3114, Buxco Electronics, Inc., Sharon, Conn.) and an esophageal pressure cannula was inserted to measure pulmonary driving pressure (pressure). The teflon tracheal tube was attached to the opening of the plethysmograph to allow the guinea pig to breathe room air from outside the chamber. The chamber was then sealed. A heating lamp was used to maintain body temperature and the guinea pig's lungs were inflated 3 times with 4 mL of air using a 10 mL calibration syringe (#5520 Series, Hans Rudolph, Kansas City, Mo.) to ensure that the lower airways had not collapsed and that the animal did not suffer from hyperventilation.

Once it was determined that baseline values were within the range 0.3-0.9 mL/cm $H_2O$ for compliance and within the range 0.1-0.199 cm $H_2O$/mL per second for resistance, the pulmonary evaluation was initiated. A Buxco pulmonary measurement computer program enabled the collection and derivation of pulmonary values. Starting this program initiated the experimental protocol and data collection. The changes in volume over time that occured within the plethysmograph with each breath were measured via a Buxco pressure transducer. By integrating this signal over time, a measurement of flow was calculated for each breath. This signal, together with the pulmonary driving pressure changes, which were collected using a Sensym pressure transducer (#TRD4100), was connected via a Buxco (MAX 2270) preamplifier to a data collection interface (#'s SFT3400 and SFT3813). All other pulmonary parameters were derived from these two inputs.

Baseline values were collected for 5 minutes, after which time the guinea pigs were challenged with Ach. Ach was infused intravenously for 1 minute from a syringe pump (sp210iw, World Precision Instruments, Inc., Sarasota, Fla.) at the following doses and prescribed times from the start of the experiment: 1.9 μg/minute at 5 minutes, 3.8 μg/minute at 10 minutes, 7.5 μg/minute at 15 minutes, 15.0 μg/minute at 20 minutes, 30 μg/minute at 25 minutes and 60 μg/minute at 30 minutes. If resistance or compliance had not returned to baseline values at 3 minutes following each Ach dose, the guinea pig's lungs were inflated 3 times with 4 mL of air from a 10 mL calibration syringe. Recorded pulmonary parameters included respiration frequency (breaths/minute), compliance (mL/cm $H_2O$) and pulmonary resistance (cm $H_2O$/mL per second) (Giles et al., 1971). Once the pulmonary function measurements were completed at minute 35 of this protocol, the guinea pig was removed from the plethysmograph and euthanized by $CO_2$ asphyxiation.

The quantity $PD_2$, which is defined as the amount of Ach needed to cause a doubling of the baseline pulmonary resistance, was calculated using the pulmonary resistance values derived from the flow and the pressure over a range of Ach challenges using the following equation. This was derived from the equation used to calculate $PC_{20}$ values in the clinic (Am. Thoracic Soc, 2000).

$$PD_2 = \text{antilog}\left[\log C_1 + \frac{(\log C_2 - \log C_1)(2R_0 - R_1)}{R_2 - R_1}\right]$$

where:

$C_1$=Second to last Ach concentration (concentration preceding $C_2$)

$C_2$=Final concentration of Ach (concentration resulting in a 2-fold increase in pulmonary resistance ($R_L$))

$R_0$=Baseline $R_L$ value $R_1$=$R_L$ value after $C_1$ $R_2$=$R_L$ value after $C_2$ Statistical analysis of the data was performed using a One-Way Analysis of Variance followed by post-hoc analysis using a Bonferroni/Dunn test. A P-value<0.05 was considered significant.

Dose-response curves were fitted with a four parameter logistic equation using GraphPad Prism, version 3.00 for Windows (GraphPad Software, San Diego, Calif.)

$$Y=\text{Min}+(\text{Max}-\text{Min})/(1+10^{((\log ED_{50}-X)* \text{Hillslope})}),$$

where X is the logarithm of dose, Y is the response ($PD_2$), and Y starts at Min and approaches asymptotically to Max with a sigmoidal shape.

Representative compounds of the invention were found to have significant bronchoprotective activity at time points beyond 24 hours post-dose.

The following synthetic examples are offered to illustrate the invention, and are not to be construed in any way as limiting the scope of the invention.

EXAMPLES

General: Unless noted otherwise, reagents, starting material and solvents were purchased from commercial suppliers, for example Sigma-Aldrich (St. Louis, Mo.), J. T. Baker (Phillipsburg, N.J.), and Honeywell Burdick. and Jackson (Muskegon, Mich.), and used without further purification; reactions were run under nitrogen atmosphere; reaction mixtures were monitored by thin layer chromatography (silica TLC), analytical high performance liquid chromatography (anal. HPLC), or mass spectrometry; reaction mixtures were commonly purified by flash column chromatography on silica gel, or by preparative HPLC using the general protocol described below; NMR samples were dissolved in deuterated solvent ($CD_3OD$, $CDCl_3$, or DMSO-d6), and spectra were acquired with a Varian Gemini 2000 instrument (300 MHz) under standard parameters; and mass spectrometric identification was performed by an electrospray ionization method (ESMS) with a Perkin Elmer instrument (PE SCIEX API 150 EX).

Example 1

Synthesis of 5-((R)-2-{2-[4-((R)-2-amino-2-phenylethylamino)-phenyl]ethylamino}-1-hydroxyethyl)-8-hydroxy-1H-quinolin-2-one a. Preparation of [2-(4-nitrophenyl)ethyl]carbamic acid tert-butyl ester Di-tert-butyl dicarbonate (20 g, 92 mmol) was suspended in saturated sodium hydrogen carbonate (200 mL) and cooled to 0° C. Dioxane (10 mL) was added. A solution of 2-(4-nitrophenyl)ethylamine hydrochloride (20 g, 99 mmol) was prepared in water (150 mL) and added dropwise. During the addition crystallization appeared to occur. After addition was complete the mixture was stirred at 0° C. for a further 15 minutes, then at room temperature for 16 hours. The product was collected by filtration and washed with 500 mL water, it was air dried.

b. Preparation of [2-(4-aminophenyl)ethyl]carbamic acid tert-butyl ester

To the partially dried cake of the previous step was added palladium on carbon (2 g, 10% Pd) followed by methanol (250 mL, under nitrogen). The atmosphere was replaced with hydrogen and the mixture stirred at atmospheric pressure for 24 hours. The palladium residue was removed by filtration and the solvent removed under reduced pressure. The title intermediate was obtained as an off-white solid (20 g, 85 mmol, 93% over two steps).

c. Preparation of (R)-{[4-(2-tert-butoxycarbonylaminoethyl) phenylcarbamoyl]phenyl-methylcarbamic acid tert-butyl ester

[2-(4-Aminophenyl)ethyl]carbamic acid tert-butyl ester (1 g, 4.2 mmol), ((R)-tert-butoxycarbonylamino)phenylacetic acid (920 mg, 3.7 mmol) and 1-hydroxybenzotriazole (600 mg, 4.4 mmol) were dissolved in N,N-dimethylformamide (10 mL) under nitrogen and cooled to 0° C. 1-(3-Dimethylaminopropyl)-3-ethylcarbodiimide hydrochloride (850 mg, 4.4 mmol) was added and the mixture stirred at 0° C. for 10 minutes, then at room temperature for 21 hours. The mixture was partitioned between water and ethyl acetate, and the organics washed with 0.5 M citric acid, saturated sodium hydrogencarbonate and saturated sodium chloride. The organics were then dried over sodium sulfate and evaporated to dryness. The title intermediate was used without further purification.

d. Preparation of (R)-2-amino-N-[4-(2-aminoethyl)phenyl]-2-phenylacetamide

The crude product of the previous step was dissolved in dichloromethane (10 mL) and trifluoroacetic acid was added (10 mL). The mixture was stirred for one hour then the volatiles were removed under reduced pressure. The oil was taken up in dichloromethane and washed with 1 N sodium hydroxide. The dichloromethane phase was dried over sodium sulfate and evaporated to dryness, giving the title intermediate (690 mg, 2.6 mmol) that was used without further purification.

e. Preparation of (R)-$N^2$-[4-(2-aminoethyl)phenyl]-1-phenylethane-1,2-diamine

The crude product of the previous step (690 mg, 2.6 mmol) was dissolved in tetrahydrofuran (7 mL) and treated with borane-dimethyl sulfide complex (1 mL). The mixture was refluxed for 5 hours and cooled to room temperature. Methanol (30 mL) was added and the mixture evaporated to dryness. Methanol (30 mL) was again added, and the mixture evaporated to dryness. The title intermediate was used without further purification.

f. Preparation of 5-((R)-2-{2-[4-((R)-2-amino-2-phenylethylamino)phenyl]ethylamino}-1-(tert-butyldimethylsilanyloxy)ethyl)-8-benzyloxy-H-quinolin-2-one Under nitrogen the crude product of the previous step (330 mg, 1.3 mmol), 8-benzyloxy-5-[(R)-2-bromo-1-(tert-butyldimethylsilanyloxy)ethyl]-1H-quinolin-2-one (490 mg, 1.0 mmol), sodium iodide (150 mg, 1.0 mmol) and sodium hydrogen carbonate (250 mg, 3.0 mmol) were treated with dimethyl sulfoxide (2.5 mL) and heated to 140° C. for 15 minutes. The mixture was cooled to room temperature and partitioned between water and ethyl acetate. The organics were washed with saturated sodium chloride, dried over sodium sulfate and evaporated to dryness. The product was purified by reverse-phase HPLC and isolated by lyophilization to give the title intermediate as its trifluoroacetate salt.

g. Preparation of 5-((R)-2-{2-[4-((R)-2-amino-2-phenylethylamino)phenyl]ethylamino}-1-hydroxyethyl)-8-benzyloxy-1H-quinolin-2-one The product of the previous step was dissolved in tetrahydrofuran (1.5 mL) and treated with triethylamine-trihydrofluoride (160 uL) for 24 hours. The mixture was partitioned between 1 N sodium hydroxide and ethyl acetate. The organics were dried over anhydrous sodium sulfate and evaporated to dryness to give the title intermediate (42 mg) which was used without further purification.

h. Synthesis of 5-((R)-2-{2-[4-((R)-2-amino-2-phenylethylamino)phenyl]ethylamino}-1-hydroxyethyl)-8-hydroxy-1H-quinolin-2-one The crude product of the previous step (42 mg) was dissolved in dichloromethane (1 mL) and boron trichloride (1.0 M in dichloromethane, 400 μL) was added. After 15 minutes, water (5 mL) and acetonitrile (500 μL) were added and the dichloromethane removed under reduced pressure. The title compound was purified by reverse-phase HPLC and isolated as its trifluoroacetate salt by lyophilization. $^1$H NMR (300 MHz, DMSO-$d_6$): 10.4 (br s, 2H), 9.2 (br s, 1H), 8.6 (br s, 3H), 8.1 (d, 1H, J=10.2 Hz), 7.2-7.4 (m, 5H), 7.0 (d, 1H, 8.2 Hz), 6.8-6.9 (m, 3H), 6.5 (d, 2H, J=8.0 Hz), 6.4 (s, 1H, J=10.2 Hz), 5.3 (br d, 1H, J=7.7 Hz), 4.3 (m, 1H), 3.4 (dd, 1H, J=7.1, 13.9 Hz), 3.3 (dd, 1H, J=6.5, 13.9 Hz), 2.8-3.0 (m, 4H), 2.6-2.8 (m, 2H). m/z: [M+H$^+$] calcd for $C_{27}H_{30}N_4O_3$: 459.2; found 459.4.

Example 2

Synthesis of N-[5-((R)-2-{2-[4-((R)-2-amino-2-phenyl-ethylamino)phenyl]ethylamino}-1-hydroxyethyl)-2-hydroxyphenyl]-formamide a. Preparation of N-[5-((R)-2-{2-[4-((R)-2-amino-2-phenyl-ethylamino)phenyl]-ethylamino}-1-(tert-butyldimethylsilanyloxy)ethyl)-2-benzyloxyphenyl]formamide Under nitrogen, crude (R)-$N^2$-[4-(2-aminoethyl)phenyl]-1-phenylethane-1,2-diamine (Example 1, step e) (320 mg, 1.3 mmol), N-[2-benzyloxy-5-((R)-2-bromo-1-(tert-butyldimethylsilanyloxy)ethyl)phenyl]formamide (450 mg, 1.0 mmol), sodium iodide (150 mg, 1.0 mmol) and potassium carbonate (550 mg, 4.0 mmol) were treated with dimethyl sulfoxide (2.5 mL) and heated to 140° C. for 15 minutes. The mixture was cooled to room temperature and partitioned between water and ethyl acetate. The organics were washed with saturated sodium chloride, dried over sodium sulfate and evaporated to dryness. The product was purified by reverse-phase HPLC and isolated by lyophilization to give the title intermediate as its trifluoroacetate salt.

b. Preparation of N-[5-((R)-2-{2-[4-((R)-2-amino-2-phenyl-ethylamino)phenyl]-ethylamino}-1-hydroxyethyl)-2-benzyloxyphenyl]formamide The product of the previous step was dissolved in tetrahydrofuran (2.0 mL) and treated with triethylamine-trihydrofluoride (200 μL) for 23 hours. The mixture was partitioned between 1 N sodium hydroxide and ethyl acetate. The organics were dried over anhydrous sodium sulfate and evaporated to dryness to give the title intermediate (55 mg), which was used without further purification.

c. Synthesis of N-[5-((R)-2-{2-[4-((R)-2-amino-2-phenyl-ethylamino)phenyl]ethylamino}-1-hydroxyethyl)-2-hydroxyphenyl]formamide To a mixture of the product of the previous step (55 mg) and palladium on carbon (10% Pd, 11 mg), methanol (2 mL) was added under nitrogen,. The suspension was stirred vigorously under hydrogen (atmospheric pressure) for 23 hours. The catalyst was removed by filtration and the solution acidified with acetic acid and diluted with water. The title compound was purified by reverse-phase HPLC and isolated as its trifluoroacetate salt by lyophilization. $^1$H NMR (300 MHz, DMSO-$d_6$): 10.0 (s, 1H), 9.5 (s, 1H), 8.5 (br s, 2H), 8.3 (br s, 3H), 8.2 (s, 1H), 8.0 (s, 1H), 7.2-7.4 (m, 5H), 6.9 (d, 2H, J=8.0 Hz), 6.8 (dd, 1H), 6.7 (d, 1H, J=8.2 Hz), 6.5 (d, 2H, J=8.2 Hz), 6.0 (m, 1H), 5.6 (m, 1H), 4.6 (m, 1H), 4.2 (m, 1H), 2.8-3 (m, 4H), 2.6-2.7 (m, 2H). m/z: [M+H$^+$] calcd for $C_{25}H_{30}N_4O_3$: 435.2; found 435.3.

Example 3

Alternative synthesis of 5-((R)-2-{2-[4-((R)-2-amino-2-phenyl-ethylamino)phenyl]ethylamino}-1-hydroxyethyl)-8-hydroxy-1H-quinolin-2-one a. Preparation of (S)-2-[4-(2-aminoethyl)phenylamino]-1-phenylethanol To a 1000 mL 3-neck flask was added 20 g (147 mmol) of 2-(4-aminophenyl)ethylamine and 30 mL of 1,3-dimethyl-3,4,5,6-tetrahydro-2(1H)pyrimidinone (DMPU). The reaction flask was fitted with an overhead stirrer and a thermometer. The reaction flask was purged with nitrogen and placed in a cold water bath. The reaction mixture was charged with 165 mL (165 mmol) of 1.0 M sodium bis(trimethylsilyl)amide in tetrahydrofuran (the temperature remained below 30° C.). The sodium bis(trimethylsilyl)amide solution was added in one portion with vigorous stirring. The reaction mixture was cooled to −10° C. and (S)-styrene oxide (17 mL, 150 mmol) was added. The rate of addition was controlled to maintain a temperature below −10° C. The reaction was allowed to warm to 20° C. within 15 minutes after the addition of (S)-styrene oxide, reaching 28° C. within 30 minutes. The reaction was cooled to 25° C., and was quenched by dropwise addition of 90 mL water. The reaction mixture was transferred to a separatory funnel, diluted with 100 mL isopropyl acetate and washed with 90 mL saturated aqueous sodium chloride. The organic layer was washed three times with a mixture of 90 mL water and 90 mL saturated aqueous sodium chloride and finally with 180 mL saturated aqueous sodium chloride. The organic layer was concentrated under vacuum. The residue was twice reconcentrated from isopropanol (100 mL portions) and then redissolved in isopropanol (500 mL) and heated to 70° C. with stirring. Concentrated hydrochloric acid (27 mL, 327 mmol) was added over two minutes. The mixture was allowed to cool to room temperature and stirred for 14 h. The precipitated product was isolated by filtration and washed with isopropanol and isopropyl acetate. The product was dried under vacuum over a 50° C. water bath for 1 h and then dissolved in 80 mL water and transferred to a separatory funnel. Isopropyl acetate (80 mL) and 10 N aqueous sodium hydroxide (40 mL, 400 mmol) were added. The separatory funnel was shaken and the phases separated. The organic layer was washed once with 40 mL saturated NaCl and dried over magnesium sulfate. The solids were collected and the filtrate was concentrated. The residue was twice reconcentrated from toluene to afford the title intermediate as an oil (14.7 g, 59 mmol, 40%).

b. Preparation of 5-((R)-2-{2-[4-((S)-2-hydroxy-2-phenyl-ethylamino)phenyl]-ethylamino}-1-(tert-butyldimethylsilanyloxy)ethyl)-8-benzyloxy-1H-quinolin-2-one Under nitrogen, (S)-2-[4-(2-aminoethyl)-phenylamino]-1-phenylethanol (1.7 g, 6.6 mmol) and 8-benzyloxy-5-[(R)-2-bromo-1-(tert-butyldimethylsilanyloxy)ethyl]-1H-quinolin-2-one (1.5 g, 3.1 mmol) were treated with dimethyl sulfoxide (4.0 mL) and heated to 120° C. for 40 minutes. The mixture was cooled slowly to room temperature and partitioned between water and ethyl acetate (after removal of some insoluble gummy residue by decantation). The organics were washed with 0.9 M sodium acetate/acetic acid, saturated sodium hydrogen carbonate and saturated sodium chloride, dried over sodium sulfate and evaporated to dryness. The title intermediate was used without further purification.

c. Preparation of 5-((R)-2-{2-[4-((R)-2-azido-2-phenylethylamino)phenyl]ethylamino}-1-(tert-butyldimethylsilanyloxy)ethyl)-8-benzyloxy-H-quinolin-2-one Under nitrogen, the product of the previous step (500 g, 0.75 mmol) was dissolved in tetrahydrofuran (9 mL) and treated with diphenylphophoryl azide (325 µL, 1.5 mmol) and 1,8-diazabicyclo[5.4.0]undec-7-ene (226 µL, 1.5 mmol). The mixture was refluxed for 3.5 hours then cooled to room temperature for 16 hours. Additional diphenylphophoryl azide (160 µL, 0.75 mmol) and 1,8-diazabicyclo[5.4.0]undec-7-ene (113 µL, 0.75 mmol) were added and the mixture refluxed for a further 3 hours, then cooled to room temperature. The mixture was partitioned between ethyl acetate and water. The organics were washed with 0.9 M sodium acetate/acetic acid, saturated sodium hydrogen carbonate and saturated sodium chloride, dried over sodium sulfate and evaporated to dryness. The product was purified by reverse-phase HPLC and isolated by lyophilization to give the title intermediate as its trifluoroacetate salt (110 mg).

d. Preparation of 5-((R)-2-{2-[4-((R)-2-azido-2-phenylethylamino)phenyl]ethylamino}-1-hydroxyethyl)-8-benzyloxy-1H-quinolin-2-one The product of the previous step (110 mg) was dissolved in tetrahydrofuran (2.0 mL) and treated with triethylamine-trihydrofluoride (200 µL) for 23 hours. The mixture was partitioned between 1 N sodium hydroxide and ethyl acetate. The organics were dried over anhydrous sodium sulfate and evaporated to dryness to give the title intermediate (50 mg), which was used without further purification.

e. Synthesis of 5-((R)-2-{2-[4-((R)-2-amino-2-phenylethylamino)phenyl]-ethylamino}-1-hydroxyethyl)-8-hydroxy-1H-quinolin-2-one To a mixture of the product of the previous step (50 mg) and palladium on carbon (10% Pd, 10 mg) was added, under nitrogen, dichloromethane (500 µL) and ethanol (500 µL). The suspension was stirred vigorously under hydrogen (atmospheric pressure) for 23 hours. Additional catalyst (10 mg) and N,N-dimethylformamide (1 mL) were added and the suspension stirred for a further 24 hours. The catalyst was removed by filtration and the mixture was concentrated under reduced pressure. The title compound was purified by reverse-phase HPLC and isolated as its trifluoroacetate salt by lyophilization.

Example 4

Alternative synthesis of N-[5-((R)-2-{2-[4-((R)-2-amino-2-phenyl-ethylamino)phenyl]ethylamino}-1-hydroxyethyl)-2-hydroxyphenyl]-formamide a. Preparation of N-[5-((R)-2-{2-[4-((S)-2-hydroxy-2-phenylethylamino)phenyl]-ethylamino}-1-(tert-butyldimethylsilanyloxy)ethyl)-2-benzyloxyphenyl]formamide Under nitrogen (S)-2-[4-(2-aminoethyl)phenylamino]-1-phenylethanol (Example 3, part a) (1.7 g, 6.6 mmol), N-[2-benzyloxy-5-((R)-2-bromo-1-(tert-butyl-dimethylsilanyloxy)ethyl)phenyl]formamide (2.4 g, 5.2 mmol), potassium carbonate (2.8 g, 20 mmol) and sodium iodide (860 mg, 5.7 mmol) were treated with dimethyl sulfoxide (4.7 mL) and heated to 140° C. for 12 minutes. The mixture was cooled to room temperature and partitioned between water and 50% ethyl acetate/isopropyl acetate (after removal of some insoluble gummy residue by decantation). The organics were washed with water, 0.9 M sodium acetate/acetic acid, saturated sodium hydrogen carbonate and saturated sodium chloride, dried over sodium sulfate and evaporated to dryness. The title intermediate was used without further purification.

b. Preparation of N-[5-((R)-2-{2-[4-((R)-2-azido-2-phenylethylamino)phenyl]-ethylamino}-1-(tert-butyldimethylsilanyloxy)ethyl)-2-benzyloxyphenyl]formamide Under nitrogen, the product of the previous step (900 mg, 1.4 mmol) was dissolved in tetrahydrofuran (9 mL) and treated with diphenylphophoryl azide (610 µL, 2.8 mmol) and 1,8-diazabicyclo[5.4.0]undec-7-ene (420 µL, 2.8 mmol). The mixture was refluxed for 3.5 hours then cooled to room temperature for 16 hours. Additional diphenylphophoryl azide (305 µL, 1.4 mmol) and 1,8-diazabicyclo[5.4.0]undec-7-ene (210 µL, 1.4 mmol) were added and the mixture refluxed for a further 3 hours, then cooled to room temperature. The mixture was partitioned between ethyl acetate and water. The organics were washed with 0.9 M sodium acetate/acetic acid, saturated sodium hydrogen carbonate and saturated sodium chloride, dried over sodium sulfate and evaporated to dryness. The product was purified by reverse-phase HPLC and isolated by lyophilization to give the title intermediate as its trifluoroacetate salt (180 mg).

c. Preparation of N-[5-((R)-2-{2-[4-((R)-2-azido-2-phenylethylamino)phenyl]-ethylamino}-1-hydroxyethyl)-2-benzyloxyphenyl]formamide The product of the previous step (130 mg) was dissolved in tetrahydrofuran (2.0 mL) and treated with triethylamine-trihydrofluoride (200 µL) for 23 hours. The mixture was partitioned between 1 N sodium hydroxide and ethyl acetate. The organics were dried over anhydrous sodium sulfate and evaporated to dryness to give the title intermediate (90 mg), which was used without further purification.

d. Synthesis of N-[5-((R)-2-{2-[4-((R)-2-amino-2-phenylethylamino)phenyl]-ethylamino}-1-hydroxyethyl)-2-hydroxyphenyl]formamide To a mixture of the product of the previous step (90 mg) and palladium on carbon (10% Pd, 18 mg) was added, under nitrogen, dichloromethane (1 mL) and ethanol (1 mL). The suspension was stirred vigorously under hydrogen (atmospheric pressure) for 23 hours. Additional catalyst (18 mg) and N,N-dimethylformamide (1 mL) were added and the suspension was stirred for an additional 24 hours. The catalyst was removed by filtration and the mixture was concentrated under reduced pressure. The title compound was purified by reverse-phase HPLC and isolated as its trifluoroacetate salt by lyophilization.

Example 5

Alternative Preparation of (R)-$N^2$-[4-(2-aminoethyl)phenyl]-1-phenylethane-1,2-diamine a. Preparation of [2-(4-aminophenyl)ethyl]carbamic acid tert-butyl ester To a suspension of 4-aminophenethylamine(65.1 g, 1.0 equiv) in dichloromethane (1.5 L) at 0° C. was added di-tert-butyl dicarbonate (99.2 g, 0.95 equiv) in dichloromethane (300 mL) dropwise. The solution was slowly warmed to room temperature and stirred for 18 hours. Water (200 mL) was added, solvents were evaporated under reduced pressure to a volume of approximately 1 L, the aqueous and organic layers were separated, and the organic layer was washed with water (200 mL) followed by saturated aqueous sodium chloride (100 mL). The organic layer was dried over anhydrous sodium sulfate (40 g). The solids were filtered and the filtrate concentrated to give crude title intermediate (100.7 g) which was suspended in a mixture of hexanes (745 mL) and ethyl acetate (150 mL). The slurry was heated until a clear solution was obtained and then the solution was slowly cooled to room temperature. The resulting cystals were filtered, washed with 10% ethyl acetate/hexanes solution (100 mL) and dried under vacuum to provide the title intermediate (55.1 g, 48% yield).

b. Preparation of (R)-{[4-(2-tert-butoxycarbonylaminoethyl) phenylcarbamoyl]phenyl-methylcarbamic acid tert-butyl ester A 1 L flask was charged with the product of the previous step (30.0 g, 1.07 equiv), ((R)-tert-butoxycarbonylamino) phenylacetic acid (30.0 g, 1.0 equiv) and a solution of 1-hydroxy-7-azabenzotriazole (16.3 g, 1.01 equiv) in N,N-dimethylformamide (240 mL). The solution was stirred until all the solids had dissolved. The solution was cooled over an ice bath for 15 minutes and 1-[3-dimethylaminopropyl]-3-ethylcarbodiimide hydrochloride (26.9 g, 1.18 equiv) was added. The reaction was stirred at 0° C. for 80 minutes. The mixture was partitioned between water and ethyl acetate, and the organic phase was washed sequentially with water, 1 N hydrochloric acid, saturated aqueous sodium bicarbonate, and saturated aqueous sodium chloride. The organic layer was dried over anhydrous sodium sulfate. The solids were filtered and the filtrate concentrated to give the title intermediate as a solid (57 g, quantitative yield) which was used without further purification.

c. Preparation of (R)-2-amino-N-[4-(2-aminoethyl)phenyl]-2-phenylacetamide

The crude product of the previous step (57 g) was combined with dichloromethane (100 mL). The mixture was cooled to 0° C. and and trifluoroacetic acid (150 mL) was added over 15 min. The mixture was stirred for 1.5 hours at room temperature then the volatiles were removed under reduced pressure. The resulting oil was taken up in dichloromethane (300 mL) and 1 N sodium hydroxide (200 mL) was added, followed by 10 N sodium hydroxide (50 mL). The layers were separated and the basic aqueous layer was extracted with dichloromethane (3×200 mL). The organic layers were combined and dried over anhydrous sodium sulfate (20 g). The solids were removed by filtration and the filtrate concentrated to afford the title intermediate (33.3 g, quantitative yield) that was used without further purification.

d. Preparation of (R)-N²-[4-(2-aminoethyl)phenyl]-1-phenylethane-1,2-diamine

The crude product of the previous step (33.3 g, 1.0 equiv) was dissolved in tetrahydrofuran (250 mL) and cooled over an ice bath. Borane-dimethyl sulfide complex (45.5 mL, 4.0 equiv) was added. The solution was heated to 65° C., stirred for 2 hours, and then cooled to 0° C. Methanol (650 mL) was added, followed by trifluoroacetic acid (5 mL) and the mixture evaporated to dryness. The residue was dissolved in methanol (200 mL), followed by trifluoroacetic acid (5 mL) and again evaporated to dryness. The residue was dissolved in methanol (150 mL) and 1 N sodium hydroxide (150 mL) was added, followed by 10 N sodium hydroxide (40 mL). The solution was concentrated to remove the organic solvent and the residual aqueous layer was extracted with dichloromethane (400 mL, followed by 3×100 mL). The organic layers were combined and dried over anhydrous sodium sulfate. The solids were removed by filtration and the filtrate concentrated to afford crude title intermediate (29.8 g).

The crude product was dissolved in ethanol (600 mL) and stirred at 80° C. for 30 minutes. A solution of L-malic acid (16.6 g, 1.06 equiv) in water (90 mL) was added, followed by ethanol (350 mL) dropwise. The mixture was stirred at 80° C. for 30 minutes and then at room temperature for 12 hours. The solids were collected by vacuum filtration, rinsed with 10% water/ethanol (130 mL) and then with ethanol (130 mL). The crystals were dried under vacuum to afford the L-malate salt of the title intermediate (38.6 g). The L-malate salt was dissolved in water (150 mL) and dichloromethane (175 mL) was added. The mixture was stirred and cooled to 0° C. and 10.0 N sodium hydroxide (50 mL) was added. The layers were separated and the aqueous layer was extracted with dichloromethane (2×175 mL). The organic layers were combined and dried over anhydrous sodium sulfate (20 g). The solids were removed by filtration and the filtrate concentrated to yield the title intermediate (24.9 g, e.e. >99%) as a colorless oil.

Example 6

Alternative Synthesis of N-[5-((R)-2-{2-[4-((R)-2-amino-2-phenyl-ethylamino)phenyl]ethylamino}-1-hydroxyethyl)-2-hydroxyphenyl]-formamide a. Preparation of N-[5-((R)-2-{2-[4-((R)-2-amino-2-phenyl-ethylamino)phenyl]-ethylamino}-1-(tert-butyldimethylsilanyloxy)ethyl)-2-benzyloxyphenyl]formamide Under nitrogen, (R)-N²-[4-(2-aminoethyl)phenyl]-1-phenylethane-1,2-diamine (Example 5) (22.4 g, 1.4 equiv), N-[2-benzyloxy-5-((R)-2-bromo-1-(tert-butyldimethylsilanyloxy)ethyl)phenyl]formamide (29.2 g, 1.0 equiv), potassium carbonate (34.7 g, 4.0 equiv) were combined with dimethyl sulfoxide (35 mL). The resulting slurry was stirred at 100° C. for 85 minutes. The mixture was cooled to room temperature and water (200 mL) and isopropyl acetate (200 mL) were added. The layers were separated and the organic layer was washed with water (200 mL) followed by aqueous saturated sodium chloride (150 mL) and dried over anhydrous magnesium sulfate (20 g). The solids were removed by filtration and the filtrate concentrated to yield crude title intermediate as an amber colored oil.

b. Preparation of N-[5-((R)-2-{2-[4-((R)-2-amino-2-phenyl-ethylamino)phenyl]-ethylamino}-1-hydroxyethyl)-2-benzyloxyphenyl]formamide The product of the previous step (50.5 g, 1.0 equiv) was dissolved in tetrahydrofuran (300 mL) and treated with triethylamine-trihydrofluoride (19.1 g, 1.5 equiv) for 12 hours at room temperature. The organic supernatant was decanted and discarded leaving a product-containing gummy solid to which was added isopropyl acetate (200 mL) followed by 1.0 N aqueous sodium hydroxide (200 mL). The mixture was stirred until most of the solid had dissolved. The top layer of the biphasic mixture was decanted and saved. Isopropyl acetate (150 mL) was added to the aqueous layer and stirred until all solids dissolved and then the biphasic mixture was combined with the reserved organic layer. The layers were separated and the basic aqueous layer was again extracted with isopropyl acetate (150 mL). The organic layers were combined and dried over anhydrous sodium sulfate. The solids were removed by filtration and the solvent evaporated to give crude title intermediate (38.3 g), as an amber colored residue.

The crude product was divided into three batches. In a representative batch, crude product (18.1 g) was solubilized in acetonitrile (125 mL) and the solution evaporated to dryness. The residue was diluted with water (40 mL), acetonitrile (20 mL), and acetic acid (4 mL). The solution was filtered, purified by preparative HPLC and clean fractions were combined and concentrated by lyophilization to provide the trifluoroacetate salt of the title intermediate as an amorphous solid. Total yield for three batches: 20 g, 34% yield.

c. Synthesis of N-[5-((R)-2-{2-[4-((R)-2-amino-2-phenylethylamino)phenyl]ethylamino}-1-hydroxyethyl)-2-hydroxyphenyl]formamide The product of the previous step (16.0 g, 1.0 equiv) was dissolved in tetrahydrofuran (640 mL) and palladium hydroxide on carbon (3.2 g, 0.2 equiv) was added under a stream of nitrogen. The solution was stirred under hydrogen for 3 to 5 hours. The reaction flask was purged with nitrogen and the reaction mixture was filtered through celite (30.0 g) and washed with tetrahydrofuran (100 mL). The solvent was removed under vacuum to yield crude title intermediate (16.0 g) as an oil.

The crude product was divided into three batches. In a representative batch, crude product (4.0 g) was solubilized in water (10 mL) and stirred for 10 minutes to dissolution. The solution was filtered, purified by preparative HPLC and clean fractions were combined and concentrated by lyophilization to provide the trifluoroacetate salt of the title intermediate as an amorphous solid. Total yield for three batches: 8.4 g, 60% yield.

Example 7

Synthesis of crystalline N-[5-((R)-2-{2-[4-((R)-2-amino-2-phenylethylamino)phenyl]ethylamino}-1-hydroxyethyl)-2-hydroxyphenyl]formamide hydrochloride a. Preparation of N-[5-((R)-2-{2-[4-((R)-2-amino-2-phenylethylamino)phenyl]-ethylamino}-1-hydroxyethyl)-2-benzyloxyphenyl]formamide freebase The trifluoroacetate salt of N-[5-((R)-2-{2-[4-((R)-2-amino-2-phenylethylamino)phenyl]-ethylamino}-1-hydroxyethyl)-2-benzyloxyphenyl]formamide (Example 6, part b) was partitioned between dichloromethane (100 mL) and 1.0 N aqueous sodium hydroxide (100 mL). The organic layer was washed with an additional 1.0 N aqueous sodium hydroxide (100 mL), followed by water (100 mL). The organic layer was dried over anhydrous sodium sulfate for 15 minutes. The solids were collected via vacuum filtration and solvents were evaporated to afford the title intermediate as an oil.

b. Preparation of N-[5-((R)-2-{2-[4-((R)-2-amino-2-phenylethylamino)phenyl]-ethylamino}-1-hydroxyethyl)-2-hydroxyphenyl]formamide freebase To the product of the previous step (1.5 g) was added palladium hydroxide 20% w/w on carbon (300 mg), followed by a 1:1 tetrahydrofuran:ethanol mixture (60 mL). The resulting slurry was stirred vigorously under hydrogen overnight. The catalyst was removed by filtration and the filtrate concentrated under vacuum to afford crude title product (1.2 g).

c. Preparation of seed crystals of N-[5-((R)-2-{2-[4-((R)-2-amino-2-phenylethylamino)phenyl]-ethylamino}-1-hydroxyethyl)-2-hydroxyphenyl]formamide hydrochloride In a round bottom flask, the freebase product of the previous step (120 mg) was stirred with isopropyl alcohol (3.6 mL) at 50° C. until the solution became homogeneous, followed by the addition of 0.5 N HCl (0.58 mL) and the solution was stirred for an additional 5 minutes at 50° C. The solution was gradually cooled to room temperature over a period of 1.5 hours and then, stirred overnight. The resulting crystals were filtered and dried under vacuum to yield the title crystalline product (78.0 mg).

d. Synthesis of crystalline N-[5-((R)-2-{2-[4-((R)-2-amino-2-phenylethylamino)phenyl]-ethylamino}-1-hydroxyethyl)-2-hydroxyphenyl]formamide hydrochloride In a round bottom flask, the freebase product of step b. (1.0 g) was dissolved in isopropyl alcohol (30 mL) at 45° C until the solution became homogeneous, followed by the addition of 0.5 N HCl (4.8 mL). The solution was heated for a few minutes and seed crystals produced in the previous step (approximately 5 mg) were added. The solution was cooled to 35° C. and stirred for 2 hours. The solution was slowly cooled to room temperature over a period of 2 hours. The resulting crystals were isolated and dried by air filtration to give the title hydrochloride salt (690 mg). Isopropyl alcohol (7 mL) and water (3.36 mL) were added and the crystals were reheated to 45° C. Isopropyl alcohol (14 mL) was added and the slurry was stirred for 1 hour. The solution was slowly cooled to room temperature and then reheated at 40° C. for 5 hours. The solution was slowly cooled to room temperature and stirred overnight. The crystals were isolated by filtration and dried in air to give the title crystalline hydrochloride salt (550 mg).

Example 8

Characterization of crystalline N-[5-((R)-2-{2-[4-((R)-2-amino-2-phenylethylamino)phenyl]ethylamino}-1-hydroxyethyl)-2-hydroxyphenyl]formamide hydrochloride A sample of the title crystalline hydrochloride salt prepared as in Example 7, part d was characterized as follows: $^1$H NMR (300 MHz): 9.5 (s, 1H), 8.2 (s, 1H), 8.0 (br s, 1H), 7.1-7.4 (m, 6H), 6.7-6.9 (m, 5H), 6.4 (d, 2H), 5.5 (br s, 2H), 4.5 (d, 1H), 4.0 (t, 1H), 3.1 (br s, 2H), 2.6-2.8 (m, 4H), 2.3 (m, 5H); m/z: [M+H]$^+$ calcd for $C_{25}H_{30}N_4O_3$: 435.4; found 435.5; Elemental analysis (wt %) calcd for $C_{25}H_{30}N_4O_3 \cdot HCl$: C, 63.8, H, 6.6, N, 11.9, O, 10.2, Cl, 7.5; found: C, 63.7, H, 6.8, N, 11.8, O, 9.7, Cl, 8.1; Water content by Karl Fisher analysis 0.9%.

The differential scanning calorimetry trace (TA instruments model DSC2010, equilibrated at 30° C. and heated at 5° C. per minute up to 300° C.) exhibited a sharp peak in endothermic heat flow between about 185° C. and about 200° C.

The powder x-ray diffraction pattern obtained with a Rigaku X-Ray Miniflex diffractometer using Cu Kα emission (30 kV, 15 mA) with a scan rate of 3° per minute and a step size of 0.03° per point is shown in the figure.

Example 9

Synthesis of N-[5-((R)-2-{2-[4-((S)-2-amino-2-phenyl-ethylamino)phenyl]ethylamino}-1-hydroxyethyl)-2-hydroxyphenyl]-formamide a. Preparation of (S)-{[4-(2-tert-butoxycarbonylaminoethyl)phenylcarbamoyl]phenyl-methylcarbamic acid tert-butyl ester

[2-(4-Aminophenyl)ethyl]carbamic acid tert-butyl ester (3.95 g, 16.7 mmol) and ((S)-tert-butoxycarbonylamino)phenylacetic acid (3.97 g, 15.7 mmol) were dissolved with a 0.5

M solution of 1-hydroxy-7-azabenzotriazole in N,N-dimethylformamide (31.76 mL) under nitrogen and cooled to 0° C. 1-(3-Dimethylaminopropyl)-3-ethylcarbodiimide hydrochloride (3.57 g, 18.6 mmol) was added and the mixture stirred at 0° C. for 10 minutes, then at room temperature for 1.5 hours. The mixture was partitioned between water and ethyl acetate, and the organics washed with 1.0 N HCl, saturated sodium hydrogencarbonate, and saturated sodium chloride. The organics were then dried over sodium sulfate and evaporated to dryness. The title intermediate was used without further purification.

b. Preparation of (S)-2-amino-N-[4-(2-aminoethyl)phenyl]-2-phenylacetamide

The crude product of the previous step was dissolved in dichloromethane (15 mL) and cooled to 0° C. Trifluoroacetic acid (15 mL) was added and the mixture was stirred for 30 min at 0° C. The solution was warmed to room temperature and stirred for 1 hour then, the volatiles were removed under reduced pressure. The oil was taken up in dichloromethane and washed with 1 N sodium hydroxide. The organic phase was dried over sodium sulfate and evaporated to dryness, giving the title intermediate (4.3 g, 16.2 mmol) that was used without further purification.

c. Preparation of (S)-$N^2$-[4-(2-aminoethyl)phenyl]-1-phenylethane-1,2-diamine

The crude product of the previous step (4.3 g, 16.2 mmol) was dissolved in tetrahydrofuran (50 mL) and treated with borane-dimethyl sulfide complex (5.7 mL). The mixture was refluxed at 65° C. for 2 hours and cooled to room temperature. Methanol (50 mL) was added over a 30 min period followed by the addition of trifluoroacetic acid (3 mL) and the mixture was evaporated to dryness. It was taken up in methanol (50 mL) and trifluoroacetic acid (1 mL) and again evaporated to dryness. The resulting oil was then dissolved with methanol (30 mL), 1.0 N sodium hydroxide (30 mL) followed by the addition of 10.0 N sodium hydroxide (5 mL). The solution was stirred for 10 min and then diluted with water and extracted with dichloromethane. The organic layer was dried under sodium sulfate and evaporated to dryness. The crude title intermediate (3.7 g, 14.4 mmol) was then dissolved in ethyl alcohol (105 mL) and heated to 80° C. A solution of D-malic acid (2.16 g, 16.1 mmol) in $H_2O$ (5.3 mL) was added to the heated solution followed by the addition of ethyl alcohol (45 mL). The solution was cooled to room temperature and stirred for 15 hours. The precipitate was filtered and partitioned between water and dichloromethane, and the organics washed with 1.0 N NaOH and saturated sodium chloride. The organics were then dried over sodium sulfate and evaporated to dryness to give the title intermediate (2.0 g, 7.8 mmol).

d. Preparation of N-[5-((R)-2-{2-[4-((S)-2-amino-2-phenylethylamino)phenyl]-ethylamino}-1-(tert-butyldimethylsilanyloxy)ethyl)-2-benzyloxyphenyl]formamide Under nitrogen the crude product of the previous step (431 mg, 1.7 mmol), N-[2-benzyloxy-5-((R)-2-bromo-1-(tert-butyldimethylsilanyloxy)ethyl)phenyl]formamide (471 mg, 1.0 mmol), and sodium hydrogen carbonate (300 mg, 3.5 mmol) were treated with dimethyl sulfoxide (1.2 mL) and heated at 100° C. for 1 hour. The mixture was cooled to room temperature and partitioned between water and ethyl acetate. The organics were washed with saturated sodium chloride, dried over sodium sulfate and evaporated to dryness. The title intermediate was used without further purification.

e. Preparation of N-[5-((R)-2-{2-[4-((S)-2-amino-2-phenylethylamino)phenyl]-ethylamino}-1-hydroxyethyl)-2-benzyloxyphenyl]formamide The product of the previous step was dissolved in tetrahydrofuran (5 mL) and treated with triethylamine-trihydrofluoride (823 μL) for 8 hours. The mixture was partitioned between 1 N sodium hydroxide and dichloromethane. The organics were dried over anhydrous sodium sulfate and evaporated to dryness. The product was purified by reverse-phase HPLC and isolated by lyophilization to give the title intermediate as its trifluoroacetate salt (150 mg, 0.2 mmol).

f. Synthesis of N-[5-((R)-2-{2-[4-((S)-2-amino-2-phenylethylamino)phenyl]-ethylamino}-1-hydroxyethyl)-2-hydroxyphenyl]formamide The product of the previous step (150 mg, 0.2 mmol) was dissolved in ethyl alcohol (5 mL) and acetic acid (5 mL) and 20% $Pd(OH)_2$ (24 mg) was added under nitrogen. The reaction flask was purged with hydrogen gas under atmospheric pressure and stirred under hydrogen for 20 hours. The catalyst was filtered and the volatiles were evaporated. The title compound was purified by reverse-phase HPLC and isolated as its trifluoroacetate salt by lyophilization (79.0 mg, 0.12 mmol). m/z: $[M+H^+]$ calcd for $C_{25}H_{30}N_4O_3$: 435.2; found 435.8.

Example 10

Synthesis of 5-((R)-2-{2-[4-((S)-2-amino-2-phenylethylamino)-phenyl]ethylamino}-1-hydroxyethyl)-8-hydroxy-1H-quinolin-2-one Using procedures similar to steps d, e, and f of Example 9, substituting 8-benzyloxy-5-[(R)-2-bromo-1-(tert-butyldimethylsilanyloxy) ethyl]-1H-quinolin-2-one for N-[2-benzyloxy-5-((R)-2-bromo-1-(tert-butyldimethylsilanyloxy)ethyl) phenyl]-formamide in step d, the trifluoroacetate salt of the title compound was obtained. m/z: $[M+H^+]$ calcd for $C_{27}H_{30}N_4O_3$: 459.2; found 459.4.

Example 11

Synthesis of 5-((R)-2-{2-[4-((R)-2-methylamino-2-phenylethylamino)phenyl]ethylamino}-1-hydroxyethyl)-8-hydroxy-1H-quinolin-2-one a. Preparation of (R)-(benzyloxycarbonylmethylamino)phenyl acetic acid (R)-(Benzyloxycarbonylamino)phenyl acetic acid (2.0 g, 7.0 mmol) was dissolved with tetrahydrofuran under nitrogen and sodium hydride (60% dispersion in mineral oil, 840 mg, 21 mmol) was added. To the solution methyl iodide (737 mg, 50 mmol) was added and the reaction was stirred for 30 minutes. Water (1 mL) was added to the reaction and the volatiles were evaporated. The product was purified by reverse-phase HPLC and isolated by lyophilization to give the title intermediate (1.66 g, 5.5 mmol).

b. Preparation of {(R)-[4-(2-tert-butoxycarbonylaminoethyl)phenylcarbamoyl]-phenylmethyl}methylcarbamic acid benzyl ester

[2-(4-Aminophenyl)ethyl]carbamic acid tert-butyl ester (1.31 g, 5.6 mmol), the product of the previous step (1.66 g, 5.6 mmol), 1-hydroxy-7-azabenzotriazole(1.46 g, 10.5 mmol) were dissolved with N,N-dimethylformamide (10 mL) under nitrogen and cooled to 0° C. 1-(3-Dimethylaminopropyl)-3-ethylcarbodiimide hydrochloride (2.02 g, 10.5 mmol) was added and the mixture was stirred at 0° C. for 10 minutes, then at room temperature for 1.5 hours. The mixture was partitioned between water and ethyl acetate, and the organics washed with 1.0 N HCl, saturated sodium hydrogencarbonate, and saturated sodium chloride. The organics were then dried over sodium sulfate and evaporated to dryness. The title intermediate was used without further purification.

c. Preparation of {(R)-[4-(2-aminoethyl)phenylcarbamoyl]phenylmethyl}methylcarbamic acid benzyl ester The crude product of the previous step was dissolved in dichloromethane (5 mL) and trifluoroacetic acid was added (5 mL). The mixture was stirred for 30 minutes, then the volatiles were removed under reduced pressure. The oil was taken up in dichloromethane and washed with 1N sodium hydroxide. The dichloromethane phase was dried over sodium sulfate and evaporated to dryness, giving the title intermediate that was used without further purification.

d. Preparation of (R)-N-[4-(2-aminoethyl)phenyl]-2-methylamino-2-phenylacetamide The crude product of the previous step (800 mg, 1.9 mmol) was dissolved with methanol (5 mL) and dichloromethane (5 mL) and 10% palladium on carbon (200 mg) was added under nitrogen. The flask was purged with hydrogen gas under atmospheric pressure, and the reaction was stirred under hydrogen gas for 2 hours. The palladium catalyst was removed by filtration and the volatiles were evaporated giving the title intermediate.

e. Preparation of (R)-$N^2$-[4-(2-aminoethyl)phenyl]-$N^1$-methyl-1-phenylethane-1,2-diamine The crude product of the previous step (523 mg, 1.84 mmol) was dissolved in tetrahydrofuran (50 mL) and treated with borane-dimethyl sulfide complex (0.7 mL). The mixture was refluxed at 65° C. for 2 hours and cooled to room temperature. Methanol (10 mL) was added followed by the addition of 4.0 N HCl in dioxane (1.4 mL) and the mixture was stirred for 10 minutes and then evaporated to dryness. The oil was taken up again in methanol (50 mL) and trifluoroacetic acid (1 mL), and evaporated to dryness. The resulting oil was then dissolved with methanol (10 mL) and KOH (10 mL of 20% solution in $H_2O$) and stirred for 10 minutes. The solution was diluted with water and extracted with dichloromethane. The organic layer was dried under sodium sulfate and evaporated to dryness. The title intermediate was obtained as an oil which was used without further purification.

f. Preparation of 5-((R)-2-{2-[4-((R)-2-methylamino-2-phenylethylamino)phenyl]-ethylamino}-1-(tert-butyldimethylsilanyloxy)ethyl)-8-benzyloxy-1H-quinolin-2-one Under nitrogen the product of the previous step (250 mg, 0.93 mmol), 8-benzyloxy-5-[(R)-2-bromo-1-(tert-butyldimethylsilanyloxy)ethyl]-1H-quinolin-2-one (454 mg, 0.93 mmol), and sodium hydrogen carbonate (234 mg, 2.8 mmol) were treated with dimethyl sulfoxide (10 mL) and heated to 100° C. for 3 hours. The mixture was cooled to room temperature and partitioned between water and ethyl acetate. The organics were washed with saturated sodium chloride, dried over sodium sulfate and evaporated to dryness. The title intermediate was used without further purification.

g. Preparation of 5-((R)-2-{2-[4-((R)-2-methylamino-2-phenylethylamino)phenyl]-ethylamino}-1-hydroxyethyl)-8-benzyloxy-1H-quinolin-2-one The product of the previous step (80 mg, 0.12 mmol) was dissolved in tetrahydrofuran (5 mL) and treated with triethylamine-trihydrofluoride (21 μL) for 5 hours. The solution was evaporated to dryness and the product was purified by reverse-phase HPLC and isolated by lyophilization to give the title intermediate as its trifluoroacetate salt.

h. Synthesis of 5-((R)-2-{2-[4-((R)-2-methylamino-2-phenylethylamino)phenyl]-ethylamino}-1-hydroxyethyl)-8-hydroxy-1H-quinolin-2-one The product of the previous step (70 mg) was dissolved in ethyl alcohol (2 mL) and 10% palladium on carbon (14 mg) was added under nitrogen. The reaction flask was purged with hydrogen gas under atmospheric pressure and stirred under hydrogen for 2 hours. The catalyst was removed by filtration and the volatiles were evaporated. The title compound was purified by reverse-phase HPLC and isolated as its trifluoroacetate salt by lyophilization (40 mg, 0.057 mmol). $^1$H NMR (300 MHz): 10.6 (br s, 2H), 9.2 (br d, 2H), 8.8 (br d, 2H), 8.2 (d, 1H, J=10.2 Hz), 7.4-7.6 (m, 5H), 7.2 (d, 1H, 8.2 Hz), 6.9-7.0 (m, 3H), 6.5-6.6 (m, 3H), 6.2 (br s, 1H,), 5.3 (br d, 1H, J=7.1 Hz), 4.3 (m, 1H), 3.6 (dd, 1H, J=7.0, 14.0 Hz), 3.3 (dd, 1H, J=6.3, 14.0 Hz), 2.8-3.0 (m, 4H), 2.6-2.8 (m, 2H), 2.4 (s, 3H). m/z: [M+H$^+$] calcd for $C_{28}H_{32}N_4O_3$: 473.3; found 473.3.

Example 12

Synthesis of N-[5-((R)-2-{2-[4-((S)-2-methylamino-2-phenyl-ethylamino)phenyl]ethylamino}-1-hydroxyethyl)-2-hydroxyphenyl]-formamide Using procedures similar to steps f, g, and h of Example 11, substituting N-[2-benzyloxy-5-((R)-2-bromo-1-(tert-butyldimethylsilanyloxy)ethyl)phenyl]formamide for 8-benzyloxy-5-[(R)-2-bromo-1-(tert-butyldimethylsilanyloxy)ethyl]-1H-quinolin-2-one in step f, the trifluoroacetate salt of the title compound was obtained. $^1$H NMR (300 MHz): 10.0 (s, 1H), 9.5 (s, 1H), 8.5 (br s, 2H), 8.5 (br s, 2H), 8.2 (s, 1H), 8.0 (s, 1H), 7.2-7.4 (m, 5H), 6.7-6.9 (m, 4H), 6.4 (d, 2H), 6.0 (m, 1H), 5.6 (m, 1H), 4.6 (m, 1H), 4.6 (m, 1H), 3.6 (dd, 1H, J=7.1, 14.0 Hz), 3.3 (dd, 1H, J=6.0, 14.0 Hz), 2.8-3 (m, 4H), 2.6-2.7 (m, 2H), 2.3 (s, 3H). m/z: [M+H$^+$] calcd for $C_{26}H_{32}N_4O_3$: 449.3; found 449.5.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto. Additionally, all publications, patents, and patent documents cited hereinabove are incorporated by reference herein in full, as though individually incorporated by reference.

What is claimed is:

1. A compound of formula (I):

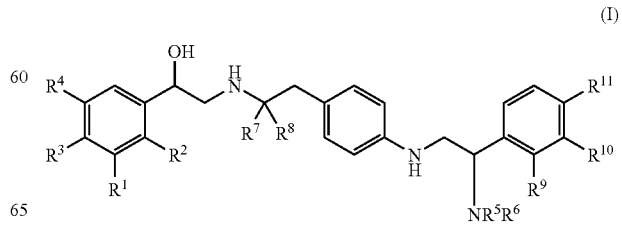

wherein:

each of $R^1$, $R^2$, $R^3$, and $R^4$ is independently selected from hydrogen, amino, halo, hydroxy, —$CH_2OH$ and —NHCHO, or $R^1$ and $R^2$ taken together are —NHC(=O)CH=CH—, or —CH=CHC(=O)NH—;

each of $R^5$ and $R^6$ is independently hydrogen or $C_{1-3}$alkyl;

each of $R^7$ and $R^8$ is independently hydrogen or $C_{1-6}$alkyl;

each of $R^9$, $R^{10}$, and $R^{11}$ is independently selected from hydrogen, halo and —$OR^a$; and $R^a$ is hydrogen or $C_{1-3}$alkyl;

or a pharmaceutically-acceptable salt or stereoisomer thereof.

2. The compound of claim 1 wherein $R^9$, $R^{10}$, and $R^{11}$ are each hydrogen.

3. The compound of claim 1 wherein $R^7$ and $R^8$ are each hydrogen.

4. The compound of claim 1 which is a compound of formula (II):

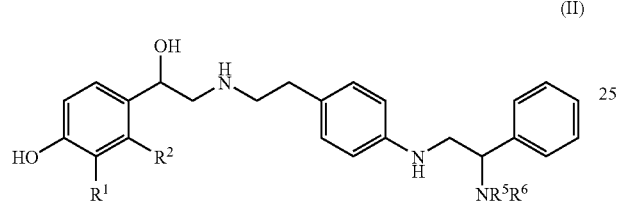

(II)

wherein:

$R^1$ is —$CH_2OH$ or —NHCHO, and $R^2$ is hydrogen; or $R^1$ and $R^2$ taken together are —NHC(=O)CH=CH— or —CH=CHC(=O)NH—;

each of $R^5$ and $R^6$ is independently hydrogen or $C_{1-3}$alkyl;

$R^a$ is hydrogen or $C_{1-3}$alkyl;

or a pharmaceutically-acceptable salt or stereoisomer thereof.

5. The compound of claim 4 wherein the stereochemistry at the alkylene carbon bearing the hydroxyl group is (R).

6. A compound selected from:

5-((R)-2-{2-[4-((R)-2-amino-2-phenylethylamino)phenyl]ethylamino}-1-hydroxy-ethyl)-8-hydroxy-1H-quinolin-2-one;

N-[5-((R)-2-{2-[4-((R)-2-amino-2-phenylethylamino)phenyl]ethylamino}-1-hydroxyethyl)-2-hydroxyphenyl]formamide;

5-((R)-2-{2-[4-((S)-2-amino-2-phenylethylamino)phenyl]ethylamino}-1-hydroxy-ethyl)-8-hydroxy-1H-quinolin-2-one;

N-[5-((R)-2-{2-[4-((S)-2-amino-2-phenylethylamino)phenyl]ethylamino}-1-hydroxyethyl)-2-hydroxyphenyl]formamide;

5-((R)-2-{2-[4-((R)-2-methylamino-2-phenylethylamino)phenyl]ethylamino}-1-hydroxyethyl)-8-hydroxy-1H-quinolin-2-one;

5-((R)-2-{2-[4-((R)-2-dimethylamino-2-phenylethylamino)phenyl]ethylamino}-1-hydroxyethyl)-8-hydroxy-1H-quinolin-2-one;

N-[5-((R)-2-{2-[4-((R)-2-methylamino-2-phenylethylamino)phenyl]ethylamino}-1-hydroxyethyl)-2-hydroxyphenyl]formamide;

N-[5-((R)-2-{2-[4-((R)-2-dimethylamino-2-phenylethylamino)phenyl]-ethylamino}-1-hydroxyethyl)-2-hydroxyphenyl]-formamide;

5-((R)-2-{2-[4-((S)-2-methylamino-2-phenylethylamino)phenyl]ethylamino}-1-hydroxyethyl)-8-hydroxy-1H-quinolin-2-one;

5-((R)-2-{2-[4-((S)-2-dimethylamino-2-phenylethylamino)phenyl]ethylamino}-1-hydroxyethyl)-8-hydroxy-1H-quinolin-2-one;

N-[5-((R)-2-{2-[4-((S)-2-methylamino-2-phenylethylamino)phenyl]ethylamino}-1-hydroxyethyl)-2-hydroxyphenyl]formamide; and N-[5-((R)-2-{2-[4-((S)-2-dimethylamino-2-phenylethylamino)phenyl]-ethylamino}-1-hydroxyethyl)-2-hydroxyphenyl]-formamide; and pharmaceutically-acceptable salts and stereoisomers thereof.

7. The compound of claim 6 which is selected from:

5-((R)-2-{2-[4-((R)-2-amino-2-phenylethylamino)phenyl]ethylamino}-1-hydroxy-ethyl)-8-hydroxy-1H-quinolin-2-one;

N-[5-((R)-2-{2-[4-((R)-2-amino-2-phenylethylamino)phenyl]ethylamino}-1-hydroxyethyl)-2-hydroxyphenyl]formamide;

5-((R)-2-{2-[4-((S)-2-amino-2-phenylethylamino)phenyl]ethylamino}-1-hydroxy-ethyl)-8-hydroxy-1H-quinolin-2-one;

N-[5-((R)-2-{2-[4-((S)-2-amino-2-phenylethylamino)phenyl]ethylamino}-1-hydroxyethyl)-2-hydroxyphenyl]formamide;

5-((R)-2-{2-[4-((R)-2-methylamino-2-phenylethylamino)phenyl]ethylamino}-1-hydroxyethyl)-8-hydroxy-1H-quinolin-2-one; and N-[5-((R)-2-{2-[4-((R)-2-methylamino-2-phenylethylamino)phenyl]ethylamino}-1-hydroxyethyl)-2-hydroxyphenyl]formamide; and pharmaceutically-acceptable salts and stereoisomers thereof.

8. Crystalline N-[5-((R)-2-{2-[4-((R)-2-amino-2-phenylethylamino)phenyl]ethylamino}-1-hydroxyethyl)-2-hydroxyphenyl]formamide hydrochloride.

9. A pharmaceutical composition comprising a therapeutically effective amount of the compound of claim 1 and a pharmaceutically acceptable carrier.

10. The pharmaceutical composition of claim 9, wherein the composition further comprises a therapeutically effective amount of one or more other therapeutic agents, wherein the other therapeutic agent is a corticosteroid or an anticholinergic agent.

11. The pharmaceutical composition of claim 9 wherein the composition is formulated for administration by inhalation.

12. A combination comprising a compound of claim 1 and a compound selected from the group consisting of (6α,11β,16α,17α)-6,9-difluoro-11-hydroxy-16-methyl-3-oxo-17-(1-oxopropoxy)androsta-1,4-diene-17-carbothioic acid S-(fluoromethyl)ester, 6α,9α-difluoro-17α-[(2-furanylcarbonyl)oxy]-11β-hydroxy-16α-methyl-3-oxo-androsta-1,4-diene-17β-carbothioic acid S-fluoromethyl ester, and 6α,9α-difluoro-11β-hydroxy-16α-methyl-3-oxo-17α-propionyloxy-androsta-1,4-diene-17β-carbothioic acid S-(2-oxo-tetrahydro-furan-3S-yl) ester.

13. A process for preparing a compound of formula (I), the process comprising:

reacting a compound of formula (III):

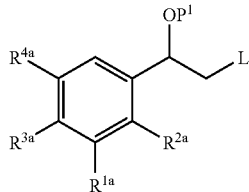

(III)

wherein $P^1$ is a hydroxy-protecting group, L is a leaving group, each of $R^{1a}$, $R^{2a}$, $R^{3a}$, and $R^{4a}$ is independently defined to be the same as $R^1$, $R^2$, $R^3$, and $R^4$ in claim 1, or —$OP^2$, wherein $P^2$ is a hydroxy-protecting group, with a compound of formula (IV):

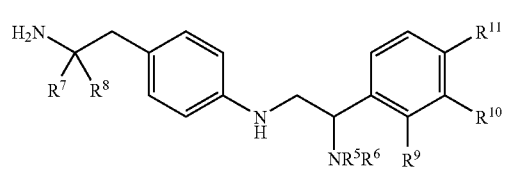

(IV)

wherein $R^5$, $R^6$, $R^7$, $R^8$, $R^9$, $R^{10}$, and $R^{11}$ are defined as in claim 1, to provide a compound of formula (V):

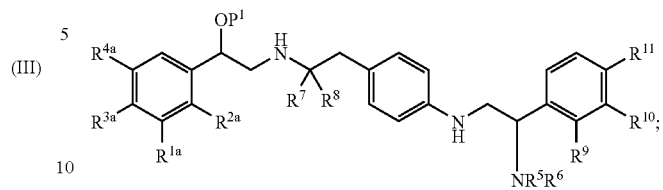

(V)

removing the protecting group $P^1$ to provide a compound of formula (VI):

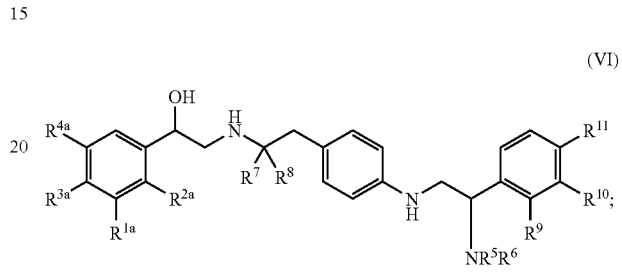

(VI)

and when any of $R^{1a}$, $R^{2a}$, $R^{3a}$, or $R^{4a}$ is —$OP^2$, removing the protecting group $P^2$ to provide a compound of formula (I), or a salt or stereoisomer thereof.

* * * * *

UNITED STATES PATENT AND TRADEMARK OFFICE
CERTIFICATE OF CORRECTION

PATENT NO. : 7,399,863 B2 Page 1 of 1
APPLICATION NO. : 10/946544
DATED : July 15, 2008
INVENTOR(S) : Linsell et al.

It is certified that error appears in the above-identified patent and that said Letters Patent is hereby corrected as shown below:

Column 3
lines 5-7, "N-{2-[4-((R)-2-hydroxy-2-phenylethylamino)phenyl]
ethyl}-(R)-2-hydroxy-2-(3-formamido-4-hydroxyphenyl)ethylamine hydrochloride"
should read "N-[5-((R)-2-{2-[4-((R)-2-amino-2-phenylethylamino)phenyl]ethylamino}-
1-hydroxyethyl)-2-hydroxyphenyl] formamide hydrochloride".

Signed and Sealed this

Sixth Day of January, 2009

JON W. DUDAS
*Director of the United States Patent and Trademark Office*